United States Patent [19]

Brieaddy et al.

[11] Patent Number: 5,723,458
[45] Date of Patent: Mar. 3, 1998

[54] HYPOLIPIDAEMIC COMPOUNDS

[75] Inventors: Lawrence Edward Brieaddy, Raleigh; Gordon Lewis Hodgson, Jr., Durham, both of N.C.

[73] Assignee: Glaxo Wellcome Inc., RTP, N.C.

[21] Appl. No.: 501,132

[22] PCT Filed: Feb. 15, 1994

[86] PCT No.: PCT/GB94/00314

§ 371 Date: Aug. 15, 1995

§ 102(e) Date: Aug. 15, 1995

[87] PCT Pub. No.: WO94/18184

PCT Pub. Date: Aug. 18, 1994

[30] Foreign Application Priority Data

Feb. 15, 1993 [GB] United Kingdom ............... 9303013
Jul. 22, 1993 [GB] United Kingdom ............... 9315155

[51] Int. Cl.$^6$ ............... C07D 285/36; C07D 513/04; C07D 281/10; A61K 31/55
[52] U.S. Cl. ............... 514/211; 540/491; 540/543; 540/552
[58] Field of Search ............... 540/491, 543, 540/552; 514/211

[56] References Cited

U.S. PATENT DOCUMENTS

| | | | |
|---|---|---|---|
| 3,362,962 | 1/1968 | Reeder et al. | 260/294.8 |
| 3,503,985 | 3/1970 | Reeder et al. | 260/294.8 |
| 3,523,974 | 8/1970 | Reeder et al. | 260/591 |
| 3,530,139 | 9/1970 | Reeder et al. | 260/294.8 |
| 3,631,089 | 12/1971 | Reeder et al. | 260/455 B |
| 4,564,612 | 1/1986 | Sugihara et al. | 514/211 |
| 5,276,025 | 1/1994 | Baldwin et al. | 514/211 |

FOREIGN PATENT DOCUMENTS

92/21668 12/1992 WIPO.

OTHER PUBLICATIONS

Sternbach et al., "A New Type of 1, 4–Benzothiazepine Derivatives," J. Org. Chem., 30(8), 2812 (1965).
Nair et al., "Synthesis & Reactions of Benz[I,4]thiazepines Derivatives," Indian J. Chem., 7(99), 862–865 (1969).
Grundy, "Cholesterol and Coronary Heart Disease," J. Amer. Med. Assn., 256(20), 2849–2859 (1986).
Sugano et al., ":Supression of Atherosclerosis in Cholesterol–Fed Rabbits by Diltiazem Injection," Arteriosclerosis, 6(2), 237–241 (1986).
"Pharmaceutical Compounds," Research Disclosure 35450, 691–693 (Oct. 1993).
Szabo et al., "Synthesis and Spectroscopic Investigation of 1,4–Benzothiazepine Derivatives," Chemical Abstracts, 108:221680x (1988).
Szabo et al., "Saturated Heterocycles. Part 116. Synthesis and Spectroscopic Investigations of 1,4–Benxothiazepine Derivatives," Heterocycles, 108:5984g (1988).

Primary Examiner—Mark L. Berch
Assistant Examiner—Bruck Kifle
Attorney, Agent, or Firm—Robert T. Hrubiec

[57] ABSTRACT

The invention provides novel 1,4-benzothiazepine compounds substituted with hydroxy or a group containing hydroxy, compositions comprising such compounds and their use in the treatment or prophylaxis of treating clinical conditions in which inhibition of bile acid uptake is indicated, for example, hyperlipidemia and atherosclerosis.

17 Claims, No Drawings

HYPOLIPIDAEMIC COMPOUNDS the present invention is concerned with new hypolipidaemic compounds, with processes and novel intermediates for their preparation, with pharmaceutical compositions containing them and with their use in medicine, particularly in the prophylaxis and treatment of hyperlipidaemic conditions, such as atherosclerosis.

Hypolipidamic conditions are often associated with elevated plasma concentrations of low density lipoprotein (LDL) cholesterol and very low density lipoprotein (VLDL) cholesterol. Such concentrations may be reduced by decreasing the absorption of bile acids from the intestine. One method by which this may be achieved is to inhibit the bile acid active uptake system in the terminal ileum. Such inhibition stimulates the conversion of cholesterol to bile acid by the liver and the resulting increase in demand for cholesterol produces a corresponding increase in the rate of clearance of LDL and VLDL cholesterol from the blood plasma or serum.

There has now been identified a novel class of heterocyclic compounds which reduce the plasma or serum concentrations of LDL and VLDL cholesterol and in consequence are particularly useful as hypolipidaemic agents. By decreasing the concentrations of cholesterol and cholesterol ester in the plasma, the compounds of the present invention retard the build-up of atherosclerotic lesions and reduce the incidence of coronary heart disease-related events. The latter are defined as cardiac events associated with increased concentrations of cholesterol and cholesterol ester in the plasma or serum.

For the purposes of this specification, a hyperlipidaemic condition is defined as any condition wherein the total cholesterol concentration (LDL+VLDL) in the plasma or serum is greater than 240 mg/dL (6.21 mmol/L) (J. Amer. Med. Assn. 256, 20, 2849–2858 (1986). U.S. Pat. No. 3,362,962 describes a genus of benzothiazepines outside the scope of the present invention which have muscle-relaxant and anticonvulsant activity; there is no disclosure in the patent specification that the compounds described therein may be useful as hypolipidaemic agents.

According to the present invention, there is provided a compound of formula (I)

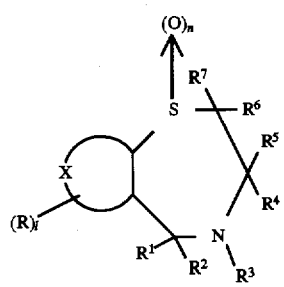

(I)

wherein
1 is an integer of from 0 to 4;
n is an integer of from 0 to 2;
R is an atom or group selected from halogen, cyano, hydroxy, nitro, alkyl, alkoxy, aryl, geteroaryl, aryloxy, arylalkoxy, aralkyl, alkaryl, $-O(CH_2)_pSO_3R^{11}$, $-O(CH_2)_pNR^{11}R^{12}$ $-O(CH_2)_pN^+R^{11}R^{12}R^{14}$, $-COR^{11}$, $-CO_2R^{11}$, $-CONR^{11}R^{12}$, $-CH_2OR^{11}$, $-NR^{11}R^{12}$, $-NHCOR^{11}$, $-NHSO_2R^{11}$, $-SR^{11}$, $-SO_2R^{11}$, $-SO_2NR^{11}R^{12}$ and $-SO_3R^{11}$ or R is a group $-OCH_2O-$ which forms a further ring attached to X wherein p is an integer of from 1 to 4, $R^{11}$ and $R^{12}$ are independently selected from hydrogen $C_{1-6}$ alkyl and phenyl and $R^{14}$ is hydrogen or $C_{1-6}$ alkyl, wherein said alkyl, alkoxy, aryl, heteroaryl, aryloxy, arylalkoxy, aralkyl and alkaryl groups are optionally substituted by one or more atoms or groups selected from halogen, hydroxy, nitro, nitrile, alkyl, alkoxy, $-COR^{11}$, $-CO_2R^{11}$, $-SO_3R^{11}$ wherein $R^{11}$ is as hereinbefore defined and $-NR^{14}R^{15}$ wherein $R^{14}$ is as hereinbefore defined and $R^{15}$ is hydrogen or $C_{1-6}$ alkyl;

$R^1$ is hydrogen or $C_{1-6}$ alkyl;

$R^2$ is an atom or group selected from hydrogen, $C_{1-6}$ alkyl (including cycloalkyl and cycloalkylalkyl), $C_{1-4}$ alkoxy, pyrryl, thienyl, pyridyl, 1,3-benzodioxolo, phenyl, and naphthyl, which groups are optionally substituted by one or more atoms or groups independently selected from halogen, cyano, hydroxy, nitro, carboxy, phenyl, phenoxy, benzyloxy, $-COR^{11}$, $-CO_2R^{11}$, $-CONR^{11}R^{12}$, $-CH_2OR^{11}$, $-NR^{11}R^{12}$, $-NHCOR^1$, $-NHSO_2R^{11}$, $-SR^{11}$, $-SO_2R^{11}$, $-SO_3R^{11}$ (wherein $R^{11}$ and $R^{12}$ are independently selected from hydrogen, $C_{1-6}$ alkyl and phenyl), $-O(CH_2)_pNR^{11}R^{12}$, $-O(CH_2)_pN^+R^{11}R^{12}R^{13}$ and $-O(CH_2)_pSO_3R^{11}$ (wherein p is an integer of from 1 to 4, $R^{11}$ and $R^{12}$ are as hereinbefore defined and $R^{13}$ is hydrogen or $C_{1-6}$ alkyl);

$R^3$ is hydrogen, hydroxy $C_{1-6}$ alkyl, alkoxy or $-O-C_{1-6}$ Acyl;

$R^4$ is a group independently selected from $C_{1-6}$ alkyl (including cycloalkyl and cycloalkylalkyl), $C_{2-6}$ alkenyl and $C_{2-6}$ alkynyl, which groups are optionally substituted by one or more atoms or groups independently selected from halogen, oxo, $-OR^{14}$, $-CO_2R^{14}$, $-NR^{14}R^{15}$, $-SR^{14}$, $-S(O)C_{1-6}$ alkyl, $-SO_2R^{14}$ and $-SO_3R^{14}$ (wherein $R^{14}$ and $R^{15}$ are as hereinbefore defined);

$R^5$ is a group independently selected from $C_{2-6}$ alkyl (including cycloalkyl and cycloalkylalkyl), $C_{2-6}$ alkenyl and $C_{2-6}$ alkynyl, which groups are optionally substituted by one or more atoms or groups independently selected from halogen, oxo, $-OR^{14}$, $-CO_2R^{14}$, $-NR^{14}R^{15}$, $-SR^{14}$, $-S(O)C_{1-6}$ alkyl, $-SO_2R^{14}$ and $-SO_3R^{14}$ (wherein $R^{14}$ and $R^{15}$ are as hereinbefore defined);

or $R^4$ and $R^5$, together with the carbon atom to which they are attached, form a $C_{3-7}$ spiro cycloalkyl group which is optionally substituted by one or more atoms or groups independently selected from halogen, $-CO_2R^{14}$, $-SO_3R^{14}$ and $-NR^{14}R^{15}$ (wherein $R^{14}$ and $R^{15}$ are as hereinbefore defined);

$R^6$ and $R^7$ are independently selected from hydrogen and $C_{1-6}$ alkyl; and X is an aromatic or non-aromatic monocyclic or bicyclic ring system having from 5 to 10 carbon atoms (including the two carbon atoms forming part of the thiazepine ring) wherein optionally one or more of the carbon atoms is/are replaced by heteroatom(s) independently selected from nitrogen, oxygen and sulphur, or X is an aromatic or non-aromatic monocyclic or bicyclic ring system having from 5 to 10 carbon atoms (including the two carbon atoms forming part of the thiazepine ring) wherein one or more of the carbon atoms is/are replaced by heteroatom(s) independently selected from nitrogen, oxygen and sulphur with the proviso that at least one of R, $R^2$, $R^4$ and $R^5$ is hydroxy or a group containing hydroxy;

and salts, solvates and physiologically functional derivatives thereof.

Preferably the present invention provides a compound of formula (Ia):

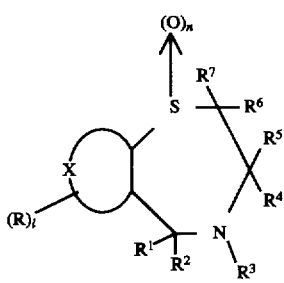

wherein
l is an integer of from 0 to 4;
n is an integer of from 0 to 2;
R is an atom or group selected from halogen, cyano, hydroxy, nitro, alkyl, alkoxy, aryl, geteroaryl, aryloxy, arylalkoxy, aralkyl, alkaryl, —$COR^{11}$, —$CO_2R^{11}$, —$CONR^{11}R^{12}$, —$CH_2OR^{11}$, —$NR^{11}R^{12}$, —$NHCOR^{11}$, —$NHSO_2R^{11}$, —$SR^{11}$, —$SO_2R^{11}$ and —$SO_3R^{11}$ wherein $R^{11}$ and $R^{12}$ are independently selected from hydrogen, $C_{1-6}$ alkyl and phenyl, wherein said alkyl, alkoxy, aryl, heteroaryl, aryloxy, arylalkoxy, aralkyl and alkaryl groups are optionally substituted by one or more atoms or groups selected from halogen, hydroxy, nitro, nitrile, alkyl, alkoxy, —$COR^{11}$, —$CO_2R^{11}$, —$SO_3R^{11}$ wherein $R^{11}$ is as hereinbefore defined and —$NR^{14}R^{15}$ wherein $R^{14}$ and $R^{15}$ are as hereinbefore defined;

$R^1$ is hydrogen or $C_{1-6}$ alkyl;

$R^2$ is an atom or group selected from hydrogen, $C_{1-6}$ alkyl (including cycloalkyl and cycloalkylalkyl), $C_{1-4}$ alkoxy, pyrryl, thienyl, pyridyl, 1,3-benzodioxolo, phenyl and napthyl, which groups are optionally substituted by one or more atoms or groups independently selected from halogen, cyano, hydroxy, nitro, carboxy, phenyl, phenoxy, benzyloxy, —$COR^{11}$, —$CO_2R^{11}$, —$CONR^{11}R^{12}$, —$CH_2OR^{11}$, —$NR^{11}R^{12}$, —$NHCOR^{11}$, —$NHSO_2R^{11}$, —$SR^{11}$, —$SO_2R^{11}$, —$SO_3R^{11}$ (wherein $R^{11}$ and $R^{12}$ are independently selected from hydrogen, $C_{1-6}$ alkyl and phenyl), —$O(CH_2)_pNR^{11}R^{12}$, —$O(CH_2)_pN^+R^{11}R^{12}R^{13}$ and —$O(CH_2)_pSO_3R^{11}$ (wherein p is an integer of from 1 to 4, $R^{11}$ and $R^{12}$ are as hereinbefore defined and $R^{13}$ is hydrogen or $C_{1-6}$ alkyl);

$R^3$ is selected from hydrogen, hydroxy and $C_{1-6}$ alkyl;

$R^4$ is a group independently selected from $C_{1-6}$ alkyl (including cycloalkyl and cycloalkylalkyl), $C_{2-6}$ alkenyl and $C_{2-6}$ alkynyl, which groups are optionally substituted by one or more atoms or groups independently selected from halogen, —$OR^{14}$, —$CO_2R^{14}$, —$NR^{14}R^{15}$ and —$SO_3R^{14}$ (wherein $R^{14}$ and $R^{15}$ are independently selected from hydrogen and $C_{1-6}$ alkyl);

$R^5$ is a group independently selected from $C_{2-6}$ alkyl (including cycloalkyl and cycloalkylalkyl), $C_{2-6}$ alkenyl and $C_{2-6}$ alkynyl, which groups are optionally substituted by one or more atoms or groups independently selected from halogen, —$OR^{14}$, —$CO_2R^{14}$, —$NR^{14}R^{15}$ and —$SO_3R^{14}$ (wherein $R^{14}$ and $R^{15}$ are independently selected from hydrogen and $C_{1-6}$ alkyl);

or $R^4$ and $R^5$, together with the carbon atom to which they are attached, form a $C_{3-7}$ spiro cycloalkyl group which is optionally substituted by one or more atoms or groups independently selected from halogen, —$OR^{14}$, —$CO_2R^{14}$, —$SO_3R^{14}$ and —$NR^{14}R^{15}$ (where $R^{14}$ and $R^{15}$ are as hereinbefore defined;

$R^6$ and $R^7$ are independently selected from hydrogen and $C_{1-6}$ alkyl; and X is an aromatic or non-aromatic monocyclic or bicyclic ring system having from 5 to 10 carbon atoms (including the two carbon atoms forming part of the thiazepine ring) wherein optionally one or more of the carbon atoms is/are replaced by heteroatom(s) independently selected from nitrogen, oxygen and sulphur, with the proviso that at least one of R, $R^2$, $R^4$ and $R^5$ is hydroxy or a group containing hydroxy;

and salts, solvates and physiologically functional derivatives thereof.

Pharmaceutically acceptable salts are particularly suitable for medical applications because of their greater aqueous solubility relative to the parent, ie basic, compounds. Such salts must clearly have a pharmaceutically acceptable anion or cation. Suitable pharmaceutically acceptable acid addition salts of the compounds of the present invention include those drived from inorganic acids, such as hydrochloric, hydrobromic, phosphoric, metaphosphoric, nitric, sulphamic and sulphuric acids, and organic acids, such as acetic, benzenesulphonic, benzoic, citric, ethanesulphonic, fumaric, gluconic, glycollic, isothionic, lactic, lactobionic, maleic, malic, methanesulphonic, succinic, p-toluenesulphonic, tartaric and trifluoroacetic acids. The chloride salt is particularly preferred for medical purposes. Suitable pharmaceutically acceptable base salts include ammonium salts, alkali metal salts, such as sodium and potassium salts, and alkaline earth salts, such as magnesium and calcium salts.

Salts having a non-pharmaceutically acceptable anion are within the scope of the invention as useful intermediates for the preparation or purification of pharmaceutically acceptable salts and/or for use in non-therapeutic, for example, in vitro, applications.

The term "physiologically functional derivative" as used herein refers to any physiologically acceptable derivative of a compound of the present invention, for example, as ester, which upon administration to a mammal, such as a human, is capable of providing (directly or indirectly) such a compound or an active metabolite thereof.

A further aspect of the present invention is prodrugs of the compounds of the invention. Such prodrugs can be metabolised in vivo to give a compound according to the invention. These prodrugs may or may not be active in their own right.

The compounds of the present invention can also exist in different polymorphic forms, for example, amorphous and crystalline polymorphic forms. All polymorphic forms of the compounds of the present invention are within the scope of the invention and are a further aspect thereof.

The term "alkyl" as used herein refers, unless otherwise stated, to a monovalent straight or branched chain radical. Likewise, the term "alkoxy" refers to a monovalent straight or branched chain radical attached to the parent molecular moiety through an oxygen atom. The term "aryl" refers to an aromatic monocyclic or bicyclic ring system comprising from 6 to 10 carbon atoms and optionally substituted by one or more atoms or groups selected from halogen, hydroxy, nitro, nitrile, alkyl, alkoxy, —$COR^{11}$, —$CO_2R^{11}$, —$SO_3R^{11}$ wherein $r^{11}$ is as hereinbefore defined and —$NR^{14}R^{15}$ wherein $R^{14}$ and $R^{15}$ are as hereinbefore defined. The term "heteroaryl" refers to an aromatic monocyclic or bicyclic ring system comprising from 5 to 10 carbon atoms wherein one or more of the carbon atoms is/are replaced by heteroatom(s) independently selected from nitrogen, oxygen and sulphur, which ring system is optionally substituted by one or more atoms or groups selected from halogen, hydroxy, nitro, nitrile, alkyl, alkoxy, —$COR^{11}$, —$CO_2R^{11}$, —$SO_3R^{11}$ wherein $R^{11}$ is as hereinbefore defined and —$NR^{14}R^{15}$ wherein $R^{14}$ and $R^{15}$ are as hereinbefore defined. The term "aryloxy" refers to an aryl group as herein defined attached to the parent molecular moiety through an oxygen atom. The term "arylalkoxy" refers to an aryl group as herein defined attached to a divalent $C_{1-6}$ alkylene group which is itself attached to the parent molecular moiety through an oxygen atom. The term "aralkyl" refers to an aryl group as herein defined attached to a divalent $C_{1-6}$ alkylene group which is itself attached to the parent molecular moiety. The term "alkaryl" refers to an alkyl group as herein defined attached to an aryl group as herein defined which is itself attached to the parent molecular moiety. The term "halogen" refers to Fluorine, Chlorine, Bromine and Iodine.

The compounds of formula (I) can exist in forms wherein one or more of the carbon centres —$C(R^6)R^7$)—, —$C(R^4)(R^5)$— and —$C(R^1)(R^2)$— is/are chiral. The present invention includes within its scope each possible optical isomer substantially free, ie associated with less than 5%, of any other optical isomer(s), and mixtures of one or more optical isomers in any proportions, including racemic mixtures.

For the purposes of this specification, the absolute chiralities of —$C(R^4)(R^5)$— and —$C(R^1)(R^2)$— are given in the order —$C(R^4)(R^5)$—, then —$C(R^1)(R^2)$—. For example, the prefix "(RS)—" denotes an (R)-configuration at —$C(R^4)(R^5)$— and an (S)-configuration at —$C(R^1)(R^2)$— and the prefix "(RS,SR)—" denotes a mixture of two isomers wherein one is (R)— at —$C(R^4)(R^5)$— and (S)— at —$C(R^1)(R^2)$— and the other is (S)— at —$C(R^4)(R^5)$— and (R)— at —$C(R^1)(R^2)$—. Other permutations will be clear to the skilled person.

In those cases where the absolute sterochemistry at —$C(R^4)(R^5)$— and —$C(R^1)(R^2)$— has not been determined, the compounds of the invention are defined in terms of the relative positions of the $R^4/R^5$ and $R^1/R^2$ substituents. Thus those compounds wherein the bulkier of the $R^4$ and $R^5$ substituents, ie the substituent of higher mass, and the bulkier of the $R^1$ and $R^2$ substituents are both located on the same side of the thiazepine ring are referred to herein as "cis", and those compounds wherein the two bulkier substituents are located on opposite sides of the ring are referred to as "trans". It will be evident to a skilled person that both "cis" and "trans" compounds of the invention can each exist in two enamtiomeric forms which are individually designated "(+)—" or "(−)—" according to the direction of rotation of a plane of polarised light when passed through a sample of the compound. Cis or trans compounds of the invention in which the individual enantiomers have not been resolved are referred to herein using the prefix "(+−)—".

Preferred compounds of formula (I) having particularly desirable hypolipidaemic properties include those wherein 1 is 0.1, or 2;
n is 1 or 2; and
$R^1$, $R^6$ and $R^7$ are all hydrogen;
$R^3$ is hydrogen or OH.

Of these, the trans isomers of those compounds wherein
(i) 1 is 0 or 1;
n is 2; and
$R^4$ and $R^5$ are groups independently selected from $C_{1-6}$ alkyl (including cycloalkyl and cycloalkylalkyl), $C_{2-6}$ alkenyl and $C_{2-6}$ alkynyl, wherein said alkyl, alkenyl, or alkynyl group may be substituted by one or more hydroxy groups, or $R^4$ and $R^5$, together with the carbon atom to which they are attached, form a $C_{3-7}$ spiro cycloalkyl group which can be substituted by one or more hydroxy groups;
(ii) 1 is 0 or 1;
n is 2; and
$R^2$ is phenyl group which may be substituted by one or more atoms or groups independently selected from halogen, cyano, hydroxy, nitro, carboxyl, phenyl, phenoxy, benzyloxy, —$COR^{11}$, —$CO_2R^{11}$, —$CONR^{11}R^{12}$, —$CH_2OR^{11}$, —$NR^{11}R^{12}$, —$NHCOR^{11}$, —$NHSO_2R^{11}$, —$SR^{11}$, —$SO_2R^{11}$, —$SO_3R^{11}$ (wherein $R^{11}$ and $R^{12}$ are independently selected from hydrogen, $C_{1-6}$ alkyl and phenyl), —$O(CH_2)_pNR^{11}R^{12}$, —$O(CH_2)_pNR^{+11}R^{12}R^{13}$ and —$O(CH_2)_pSO_3R^{11}$ (wherein p is an integer of from 1 to 4, $R^{11}$ and $R^{12}$ are as hereinbefore defined and $R^{13}$ is hydrogen or $C_{1-6}$ alkyl);
$R^4$ and $R^5$ are groups independently selected from $C_{1-6}$ alkyl (including cycloalkyl and cycloalkylalkyl), $C_{2-6}$ alkenyl and $C_{2-6}$ alkynyl, wherein said alkyl, alkenyl, or alkynyl group may be substituted by one or more hydroxy groups, or $R^4$ and $R^5$, together with the carbon atom to which they are attached, form a $C_{3-7}$ spiro cycloalkyl group which can be substituted by one or more hydroxy groups; and
(iii) 1 is 0 or 1;
n is 2;
$R^2$ is a phenyl group which may be substituted by one or more atoms or groups independently selected from halogen, cyano, hydroxy, nitro, carboxyl, phenyl, phenoxy, benzyloxy, —$COR^{11}$, —$CO_2R^{11}$, —$CONR^{11}R^{12}$, —$CH_2OR^{11}$, —$NR^{11}R^{12}$, —$NHCOR^{11}$, —$NHSO_2R^{11}$, —$SR^{11}$, —$SO_2R^{11}$, —$SO_3R^{11}$ (wherein $R^{11}$ and $R^{12}$ are independently selected from hydrogen, $C_{1-6}$ alkyl and phenyl), —$O(CH_2)_pNR^{11}R^{12}$, —$O(CH_2)_pNR^{+11}R^{12}R^{13}$ and —$O(CH_2)_pSO_3R^{11}$ (wherein p is an integer of from 1 to 4, $R^{11}$ and $R^{12}$ are as hereinbefore defined and $R^{13}$ is hydrogen or $C_{1-6}$ alkyl);
$R^4$ and $R^5$ are groups independently selected from $C_{1-6}$ alkyl (including cycloalkyl and cycloalkylalkyl), $C_{2-6}$ alkenyl and $C_{2-6}$ alkynyl, which groups can be substituted by one or more hydroxy groups; and
X is a fused phenyl, naphthyl, pyrryl, thienyl, or pyridyl group;
are particularly preferred.

Compounds of formula (I) having exceptional hypolipidaemic properties include:
(+−)-trans-3-ethyl-2,3,4,5-tetrahydro-3-((2R)-2-hydroxybutyl)-5-phenyl-1,4-benzothiazepine 1,1-dioxide;
(+−)-trans-1-(3-ethyl-2,3,4,5-tetrahydro-8-methoxy-5-phenyl-1,4-benzothiazepin-3-yl-2(R)-2-butanol S,S-dioxide;
(+−)-trans-1-(3-ethyl-2,3,4,5-tetrahydro-8-methoxy-5-phenyl-1,4-benzothiazepin-3-yl)-3-butanol S,S-dioxide;
(+−)-trans-1-(3-ethyl-2,3,4,5-tetrahydro-7-methoxy-5-phenyl-1,4-benzothiazepin-3-yl)-2(R)-2-butanol S,S-dioxide;
(+−)-trans-1-(3-ethyl-5-(4-fluorophenyl)-2,3,4,5-tetrahydro-7-methoxy-1,4-benzothiazepin-3-yl)-2(R)-2-butanol S,S-dioxide;
(+−)-trans-1-(3-ethyl-5-(4-hydroxyphenyl)-2,3,4,5-tetrahydro-1,4-benzothiazepin-3-yl)-2(R)-2-butanol S,S-dioxide 0.5 hydrate;
(+−)-trans-3-butyl-3-ethyl-2,3,4,5-tetrahydro-5-(4-hydroxyphenyl)-1,4-benzothiazepine 1,1-dioxide hydrochloride;
(+−)-cis-3-ethyl-2,3,4,5-tetrahydro-3-(4-hydroxybutyl)-5-phenyl-1,4-benzothiazepine 1,1-dioxide hydrochloride;
(+−)-trans-3-ethyl-2,3,4,5-tetrahydro-3-(4-hydroxybutyl)-5-phenyl-1,4-benzothiazepine 1,1-dioxide;
(+−)-trans-3-butyl-3-ethyl-2,3,4,5-tetrahydro-7-hydroxy-5-phenyl-1,4-benzothiazepine 1,1-dioxide;
(+−)-trans-1-(3-ethyl-2,3,4,5-tetrahydro-5-phenyl-1,4-benzothiazepin-3-yl)-4,4, 4-trifluoro-(2S)-2-butanol-S,S-dioxide;

(+−)-trans-1-(3-ethyl-2,3,4,5-tetrahydro-7-methoxy-5-phenyl-1,4-benzothiazepin-3-yl)-4,4,4-trifluoro-(2S)-2-butanol-S,S-dioxide;

(+−)-trans-3-Ethyl-2,3,4,5-tetrahydro-3-(3-hydroxybutyl)-5-phenyl-1,4-benzothiazepine 1,1-dioxide;

(+−)-trans-3-Ethyl-2,3,4,5-tetrahydro-3-(2(R)-2-hydroxybutyl)-5-(4-hydroxyphenyl)-1,4-benzothiazepine 1,1-dioxide;

(+−)-trans-1-(3-Ethyl-5-(4-fluorophenyl)-2,3,4,5-tetrahydro-1,4-benzothiazepin-3-yl)-2(R)-2-butanol S,S-dioxide;

(+−)-trans-1-(3-Ethyl-2,3,4,5-tetrahydro-7-methoxy-5-phenyl-1,4-benzothiazepin-3-yl)-4,4,4-trifluoro-2(S)-2-butanol S,S-dioxide;

(+−)-trans-1-(3-Ethyl-2,3,4,5-tetrahydro-8-methoxy-5-phenyl-1,4-benzothiazepin-3-yl)-4,4,4-trifluoro-2(S)-butanol S,S-dioxide;

(+−)-trans-1-(3-ethyl-2,3,4,5-tetrahydro-7,8-dimethoxy-5-phenyl-1,4-benzothiazepin-3-yl-2(R)-2-butanol S,S-dioxide;

(+−)-trans-1-(3-Ethyl-2,3,4,5-tetrahydro-7,8-dimethoxy-5-phenyl-1,4-benzothiazepin-3-yl)-4,4,4-trifluoro-2-butanol S,S-dioxide;

(+−)-trans-1-(3-Ethyl-2,3,4,5-tetrahydro-7,8-dimethoxy-5-phenyl-1,4-benzothiazepin-3-yl)-3,3,4,4,4-pentafluoro-2-butanol S,S-dioxide;

(+−)-trans-3-(3-ethyl-2,3,4,5-tetrahydro-5-phenyl-3-(4,4,4-trifluoro-2-hydroxybutyl)-1,4-benzothiazepin-8-yl)oxy)propanesulfonic acid 1,1-dioxide;

(+−)-trans-3-((3-ethyl-2,3,4,5-tetrahydro-3-(2-hydroxybutyl)-5-phenyl-1,4-benzothiazepin-8-yl)oxy)ethyltrimethylammonium iodide 1,1-dioxide;

(+−)-trans-1-(3-Ethyl-2,3,4,5-tetrahydro-7,8-diethoxy-5-phenyl-1,4-benzothiazepin-3-yl)-4,4,4-trifluoro-2-butanol S,S-dioxide;

(+−)-trans-3-((ethyl-2,3,4,5-tetrahydro-5-phenyl-3(4,4,4-trifluoro-2-hydroxybutyl)-1,4-benzothiazepin-8-yl)oxy)ethyltrimethylammonium iodide 1,1-dioxide;

(+−)-trans-3-((3-ethyl-2,3,4,5-tetrahydro-3-(2-hydroxybutyl)-5-phenyl-1,4-benzothiazepin-8-yl)oxy)propanesulfonic acid 1,1-dioxide;

(+−)-trans-1-(3-ethyl-2,3,4,5-tetrahydro-7,8-diethoxy-5-phenyl-1,4-benzothiazepin-3-yl)-2-butanol S,S-dioxide;

(+−)-trans-1-(3-(2,2,2-trifluoroethyl)-2,3,4,5-tetrahydro-7,8-dimethoxy-5-phenyl-1,4-benzothiazepin-3-yl)-4,4,4-trifluoro-2-butanol S,S-dioxide;

(+−)-trans-1-(3-Ethyl-2,3,4,5-tetrahydro-7,8-dihydroxy-5-phenyl-1,4-benzothiazepin-3-yl)-4,4,4-trifluoro-2-butanol S,S-dioxide;

(+−)-trans-1-(3-ethyl-2,3,4,5-tetrahydro-7,8-dimethoxy-5-phenyl-1,4-benzothiazepin-3-yl)-1-butanol S,S-dioxide;

(+−)-trans-1-(3-Ethyl-2,3,4,5-tetrahydro-7,8-dihydroxy-5-phenyl-1,4-benzothiazepin-3-yl)-2-butanol S,S-dioxide;

(+−)-trans-1-(3-ethyl-2,3,4,5-tetrahydro-8-methoxy-5-phenyl-1,4-benzothiazepin-3-yl)-4,4,4-trifluoro-1-butanol S,S-dioxide;

(+−)-trans-1-(3-ethyl-2,3,4,5-tetrahydro-7,8-dihydroxy-5-phenyl-1,4-benzothiazepin-3-yl)-2-butanone S,S-dioxide;

Of the above the following compounds are most preferred:

(+−)-trans-1-(3-ethyl-5-(4-fluorophenyl)-2,3,4,5-tetrahydro-7-methoxy-1,4-benzothiazepin-3-yl)-2(R)-2-butanol S,S-dioxide;

(+−)-trans-1-(3-ethyl-2,3,4,5-tetrahydro-5-phenyl-1,4-benzothiazepin-3-yl)-4,4,4-trifluoro-(2S)-2-butanol-S,S-dioxide;

(+−)-trans-1-(3-ethyl-2,3,4,5-tetrahydro-7-methoxy-5-phenyl-1,4-benzothiazepin-3-yl)-4,4,4-trifluoro-(2S)-2-butanol-S,S-dioxide;

(+−)-trans-1-(3-Ethyl-2,3,4,5-tetrahydro-8-methoxy-5-phenyl-1,4-benzothiazepin-3-yl)-4,4,4-trifluoro-2(S)-butanol S,S-dioxide;

(+−)-trans-1-(3-ethyl-2,3,4,5-tetrahydro-7,8-dimethoxy-5-phenyl-1,4-benzothiazepin-3-yl-2(R)-2-butanol S,S-dioxide;

According to further aspects of the invention, there are also provided:

(a) compounds of formula (I) and pharmaceutically acceptable salts, solvates and physiologically functional derivatives thereof for use as therapeutic agents, particularly in the prophylaxis and treatment of clinical conditions for which a bile acid uptake inhibitor is indicated, for example, a hyperlipidaemic condition such as atherosclerosis;

(b) pharmaceutical compositions comprising a compound of formula (I) and/or one of its pharmaceutically acceptable salts, solvates, or physiologically functional derivatives, at least one pharmaceutically acceptable carrier and, optionally, one or more other physiologically active agents;

(c) the use of a compound of formula (I) or of a pharmaceutically acceptable salt, solvate, or physiologically functional derivative thereof in the manufacture of a medicament for the prophylaxis or treatment of a clinical condition for which a bile acid uptake inhibitor is indicated, for example, a hyperlipidaemic condition, such as atherosclerosis;

(d) a method of inhibiting the absorption of bile acids from the intestine of a mammal, such as a human, which comprises administering an effective bile acid absorption inhibiting amount of a compound of formula (I) or of a pharmaceutically acceptable salt, solvate, or physiologically functional derivative thereof to the mammal;

(e) a method of reducing the blood plasma or serum concentrations of LDL or VLDL cholesterol in a mammal, such as a human, which comprises administering an effective cholesterol reducing amount of a compound of formula (I) or of a pharmaceutically acceptable salt, solvate, or physiologically functional derivative thereof to the mammal;

(f) a method of reducing the concentrations of cholesterol and cholesterol ester in the blood plasma or serum of a mammal, such as a human, which comprises administering an effective cholesterol and cholesterol ester reducing amount of a compound of formula (I) or of a pharmaceutically acceptable salt, solvate, or physiologically functional derivative thereof to the mammal;

(g) a method of increasing the faecal excretion of bile acids in a mammal, such as a human, which comprises administering an effective bile acid faecal excretion increasing amount of a compound of formula (I) or of a pharmaceutically acceptable salt, solvate, or physiologically functional derivative thereof to the mammal;

(h) a method for the prophylaxis or treatment of a clinical condition in a mammal, such as a human, for which a bile acid uptake inhibitor is indicated, for example, a hyperlipidaemic condition, such as atherosclerosis, which comprises administering a therapeutically effective amount of a compound of the formula (I) or of a pharmaceutically acceptable salt, solvate, or physiologically functional derivative thereof to the mammal;

(i) a method of reducing the incidence of coronary heart disease-related events in a mammal, such as a human, which comprises administering an effective coronary heart disease-related events reducing amount of a compound of formula (I) or of a pharmaceutically acceptable salt, solvate, or physiologically functional derivative thereof;

(j) a method of reducing the conventration of cholesterol in the blood plasma or serum of a mammal, such as a human, which comprises administering an effective cholesterol reducing amount of a compound of formula (I);

(k) processes for the preparation of compounds of formula (I) (including salts, solvates and physiologically functional derivatives thereof as defined herein); and (l) compounds of formula (II) for use as intermediates in the preparation of compounds of formula (I).

Hereinafter all reference to "compound(s) of formula (I)" refer to compound)s) of formula (I) as described above together with their salts, solvates and physiologically functional derivatives as defined herein.

The amount of a compound of formula (I) which is required to achieve the desired biological effect will, of course, depend on a number of factors, for example, the specific compound chosen, the use for which it is intended, the mode of administration and the clinical condition of the recipient. In general, a daily dose is in the range of from 0.0001 mg to 100 mg, typically from 0.0001 to 5 mg, per day per kilogram body weight, for example 0.005–0.5 mg/kg/day, preferebly 0.001 to 0.5 mg/kg/day. An intravenous dose can, for example, be in the range of from 0.001 mg to 0.5 mg/kg, which can conveniently be administered as an infusion of from 0.03 ng to 50 ng per kilogram per minute. Infusion fluids suitable for this purpose can contain, for example, from 0.0003 ng to 5 mg, typically from 0.003 ng to 5 mg, per millilitre. Unit does can contain, for example, from 0.01 mg to 10 mg of the active compound, preferably from 0.1 to 5 mg. Thus ampoules for injection can contain, for example, from 0.01 mg to 100 mg and orally administrable unit does formulations, such as tablets or capsules, may contain, for example, from 0.01 mg to 1000 mg, typically from 0.01 mg to 60 mg, preferably 0.1 mg to 10 mg. In the case of pharmaceutically acceptable salts, the weights indicated above refer to the weight of the benzothiazepine ion derived from the salt.

For the prophylaxis or treatment of the conditions referred to above, the compounds of formula (I) can be used as the compound per se, but are preferably presented with an acceptable carrier in the form of a pharmaceutical composition. The carrier must, of course, be acceptable in the sense of being compatible with the other ingredients of the composition and must not be deleterious to the recipient. The carrier can be a solid or a liquid, or both, and is preferably formulated with the compound as a unit-dose composition, for example, a tablet, which can contain from 0.05% to 95% by weight of the active compound. Other pharmacologically active substances can also be present including other compounds of formula (I). The pharmaceutical compositions of the invention van be prepared by any of the well known techniques of pharmacy consisting essentially of admixing the components.

Pharmaceutical compositions according to the present invention include those suitable for oral, rectal, topical, buccal (e.g. sub-lingual) and parenteral (e.g. subcutaneous, intramuscular, intradermal, or intravenous) administration, although the most suitable route in any given case will depend on the nature and severity of the condition being treated and on the nature of the particular compound of formula (I) which is being used. Enteric-coated and enteric-coated controlled release formulations are also within the scope of the invention. Suitable enteric coatings include cellulose acetate phthalate, polyvinylacetate phthalate, hydroxypropylmethylcellulose phthalate and anionic polymers of methacrylic acid and methacrylic acid methyl ester.

Pharmaceutical compositions suitable for oral administration can be presented in discrete units, such as capsules, cachets, lozenges, or tablets, each containing a predetermined amount of a compound of formula (I); as a powder or granules; as a solution or a suspension in an aqueous or non-aqueous liquid; or as an oil-in-water or water-in-oil emulsion. As indicated, such compositions can be prepared by any suitable method of pharmacy which includes the step of bringing into association the active compound and the carrier (which can constitute one or more accessory ingredients). In general, the compositions are prepared by uniformly and intimately admixing the active compound with a liquid or finely divided solid carrier, or both, and then, if necessary, shaping the product. For example, a table can be prepared by compressing or moulding a powder or granules of the compound, optionally with one or more assessory ingredients. Compressed tablets can be prepared by compressing, in a suitable machine, the compound in a free-flowing form, such as a powder or granules optionally mixed with a binder, lubricant, inert diluent and/or surface active/dispersing agent(s). Moulded tablets can be made by moulding, in a suitable machine, the powdered compound moistened with an inert liquid diluent.

Pharmaceutical compositions suitable for buccal (sublingual) administration include lozenges comprising a compound of formula (I) in a flavoured base, usually sucrose and acacia or tragacanth, and pastilles comprising the compound in an inert base such as gelatin and glycerin or sucrose and acacia.

Pharmaceutical compositions suitable for parenteral administration conveniently comprise sterile aqueous preparations of a compound of formula (I), preferably isotonic with the blood of the intended recipient. These preparations are preferably administered intravenously, although administration can also be effected by means of subcutaneous, intramuscular, or intradermal injection. Such preparations can conveniently be prepared by admixing the compound with water and rendering the resulting solution sterile and isotonic with the blood. Injectable compositions according to the invention will generally contain from 0.1 to 5% w/w of the active compound.

Pharmaceutical compositions suitable for rectal administration are preferably presented as unit-dose suppositories. These can be prepared by admixing a compound of formula (I) with one or more conventional solid carriers, for example, cocoa butter, and then shaping the resulting mixture.

Pharmaceutical compositions suitable for topical application to the skin preferably take the form of an ointment, cream, lotion, paste, gel, spray, aerosol, or oil. Carriers which can be used include vaseline, lanoline, polyethylene glycols, alcohols, and combinations of two or more thereof. The active compound is generally present at a concentration of from 0.1 to 15% w/w of the composition, for example, from 0.5 to 2%.

Transdermal administration is also possible. Pharmaceutical compositions suitable for transdermal administration can be presented as discrete patches adapted to remain in intimate contact with the epidermis of the recipient for aprolonged period of time. Such patches typically contain the active compound in an optionally buffered, aqueous solution, dissolved and/or dispersed in an adhesive, or dispersed in a polymer. A suitable concentration of the active compound is about 1% to 35%, preferably about 3% to 15%. As one particular possibility, the active compound can be delivered from the patch by electrotransport or iontophoresis, for example, as described in *Pharmaceutical Research*, 3(6), 318 (1986).

The compounds of the invention can be prepared by conventional methods known to a skilled person or in an analogous manner to processes described in the art.

For example, compounds of formula (I) wherein n=O and $R^1$ and $R^3$ are hydrogen can be prepared by reducing the imine bond of a compound of formula (II)

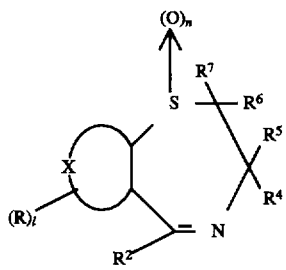
(II)

wherein 1, R, $R^2$, $R^4$ to $R^7$ and X are as hereinbefore defined, using, for example, a metal hydride compound, such as borane, in a suitable solvent, such as THF, or when n=1 or 2 in formula (I) catalytic hydrogenation using, for example, a palladium catalyst, such as 10% Pd/C.

Compounds of formula (II) are herein defined are considered to be novel and constitute a further aspect of the present invention.

Compounds of formula (II) can be prepared by cyclising compounds of formula (III)

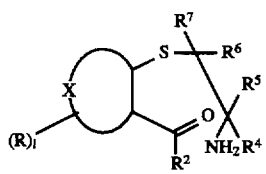
(III)

wherein 1, R, $R^2$, $R^4$ to $R^7$ and X are to hereinbefore defined, by, for example, azeotropic distillation or refluxing in the presence of a suitable drying agent, such as molecular sieves, in a suitable solvent, for example, 2,6-lutidine, in the presence of an acid, such as HCl.

Compounds of formula (III) can be prepared by reacting a compound of formula (IV)

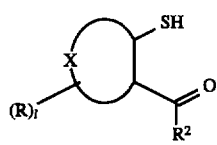
(IV)

wherein 1, R, $R^2$ and X are as hereinbefore defined, with a compound of formula (V), or preferably with a compound of formula (Va)

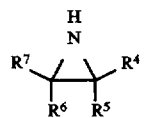
(V)

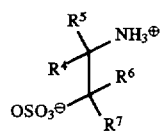
(Va)

wherein $R^4$ to $R^7$ are as hereinbefore defined, typically in a polar solvent, for example, methanol.

Compounds of formula (IV) can be prepared by hydrolysis of a compound of formula (XXII)

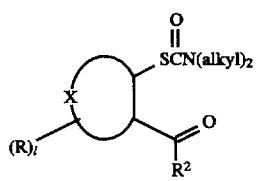
(XXII)

wherein 1, X, R and $R^2$ are as hereinbefore defined with, for example, a base, such as KOH in a suitable solvent such as methanol/THF.

Compounds of formula (XXII) can be prepared by heating a compound of formula (XXIII)

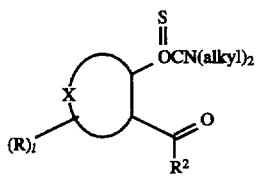
(XXIII)

wherein 1 X, R and $R^2$ are as hereinbefore defined in a non-polar solvent such as $(PH)_2O$.

Compounds of formula (XXIII) can be prepared by reaction of a compound of formula (XXIV)

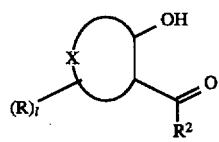
(XXIV)

wherein 1, X, R and $R^2$ are as hereinbefore defined with halo-CSN(alkyl)$_2$, for example, ClCSNMe$_2$ in a suitable solvent such as DMAP/Et$_3$N.

Compounds of formula (III) can also be prepared by reacting a compound of formula (XVIII)

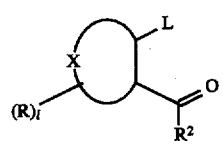
(XVIII)

wherein 1, R, $R^2$ and X are as hereinbefore defined and L is a suitable leaving group, for example, halogen, with a compound of formula $HSC(R^6)(R^7)C(R^4)(R^5)NH_2$ wherein $R^4$ to $R^7$ are as hereinbefore defined.

Compounds of formula (XVIII) can be prepared by reacting a compound of formula (XIX)

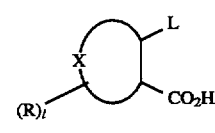
(XIX)

wherein 1, L, R and X are as hereinbefore defined, with a compound of formula $R^2H$ wherein $R^2$ is as hereinbefore defined, typically by a Friedel-Crafts reaction using, for example, aluminum chloride.

Alternatively, compounds of formula (XVIII) can be prepared by reacting a compound of formula (XVIIIa)

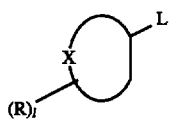 (XVIIIa)

wherein 1, L, R and X are as hereinbefore defined with a suitable acid halide, e.g. R²COCl wherein R² is as hereinbefore defined, by a Friedel-Gafts reaction using, for example, aluminium chloride.

Compounds of formula (III) wherein R⁴ is —CH₂OH can also be prepared by hydrolysis, preferably with base, of a compound of formula (XVII)

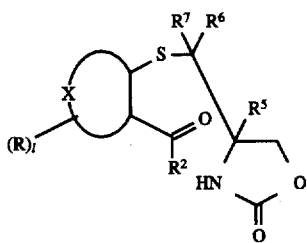 (XVII)

where 1, R² R⁵ to R⁷ and X are at hereinbefore defined, using, for example, KOH in aqe. ethanol.

Compounds of formula (XVII) can be prepared by reacting a compound of formula (IV) wherein m, R, R² and X are as hereinbefore defined, with a compound of formula (XII)

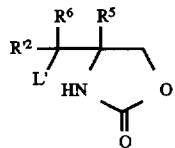 (XII)

wherein R⁵ to R⁷ are as hereinbefore defined and L' is a suitable leaving group, for example, —OTosyl, typically in a polar aprotic solvent, such as DMF, in the presence of a base, for example, NaH.

Compounds of formula (IV) can be prepared by reacting a compound of formula (VI)

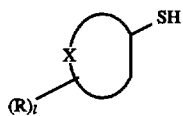 VI wherein 1, R and X are as hereinbefore defined, with a compound of formula R²CN wherein R² is as hereinbefore defined. The reaction is typically carried out by metalation of compound (VI) using, for example, n-butyl lithium in the presence of N,N,N',N'-tetramethylethylenediamine (TMEDA) followed by reaction with the appropriate nitrile in a non-polar solvent for example, cyclohexane.

Compounds of formula (IV) can also be prepared by reacting a compound of formula (XVIII) as hereinbefore defined with sodium sulphide (NaSH) on metalation when L is halogen followed by reaction with sulphur.

Alternatively, compounds of formula (IV) can be prepared from a compound of formula (XVIIIb)

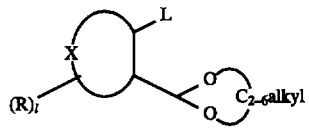 (XVIIIb)

wherein 1, R, R², X and L are as hereinbefore defined and preferably C₂₋₆ alkyl is —CH₂—CH₂— or —CH₂—C(Me)₂—CH₂—, by metalation of a compound of formula (XVIIIa) using, for example, magnesium or n-butyllithium followed by reaction with sulphur (S₈) and hydrolysis of the alkylenedioxy protecting group with, for example, acid.

Compounds of formula (XVIIIb) can be prepared from the corresponding compounds of formula (XVIII) by reaction with the appropriate C₂₋₆ diol, preferably 1,2-ethanediol or 2,2-dimethyl-1,3-propanediol in a suitable solvent, for example toluene and preferably in the presence of a catalyst such as p-toluenesulfonic acid.

Compounds of formulae (V), (Va), (XIX), (VI) and R²CN as hereinbefore defined can be obtained commercially or prepared by methods known to those skilled in the art or obtainable from the chemical literature. Thus compounds of formula (V) can be prepared from the corresponding 2-substituted 2-aminoethanols or from compounds of formula (Va) and compounds of formula (XII) from the corresponding 2-substituted-2-amino-1,3-propanediols. 2-substituted-2-aminoethanols and 2-substituted-2-amino-1,3-propanediols can be obtained commercially or prepared by methods known to those skilled in the art or obtainable from the chemical literature.

Compounds of formula (I) wherein n=0 and R¹ is not hydrogen can be obtained by reacting the corresponding compound of formula (II) with, for example, an organometallic compound, such as R¹Li, R¹Cu, R¹Zn, or R¹MgBr wherein R¹ is as hereinbefore defined other than hydrogen.

Compounds of formula (I) wherein n=0 and R³ is hydrogen can also be prepared by cyclising a compound of formula (VIII)

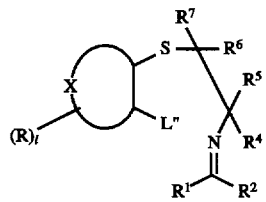 (VIII)

wherein 1, R, R¹, R², R⁴ to R⁷ and X are as hereinbefore defined and L" is halogen, for example, bromine, by treatment with strong base, for example, n-butyl lithium, in a suitable solvent, such as THF, at a low temperature, for example, −78° C.

Compounds of formula (VIII) can be prepared by reaction of a compound of formula (IX)

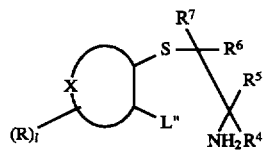 (IX)

wherein 1, L", R, R⁴ to R⁷ and X are as hereinbefore defined, with a compound of formula R¹R²C=O wherein R¹ and R² are as hereinbefore defined. The reaction is typically carried out in a non-polar solvent, for example, toluene, in the presence of an acid, such as p-toluenesulphonic acid.

Compounds of formula (IX) can be prepared by reacting a compound of formula (XI)

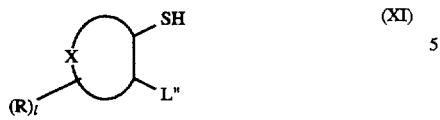

wherein 1, L", R and X are as hereinbefore defined, with a compound of formula (V) wherein $R^4$ to $R^7$ are as hereinbefore defined, typically in a polar solvent, such as methanol.

Compounds of formula (IX) can also be prepared by reacting a compound of formula (XI) as hereinbefore defined with a compound of formula (XX)

wherein $R^4$ to $R^7$ are as hereinbefore defined, in the presence of a Lewis acid, for example, lithium chloride, at an elevated temperature, such as 170°–210° C.

Compounds of formulae $R^1R^2C=O$ as hereinbefore defined, (XI) and (XX) can be obtained commercially or prepared by methods known to those skilled in the art or obtainable from the chemical literature. Thus compounds of formula (XI) can be prepared from the corresponding disulphides and compounds of formula (XX) from the corresponding 2-substituted 2-aminoethanols.

Compounds of formula (I) wherein n=0 and $R^1$ and $R^3$ are both hydrogen can also be obtained by reacting a compound of formula (XIII)

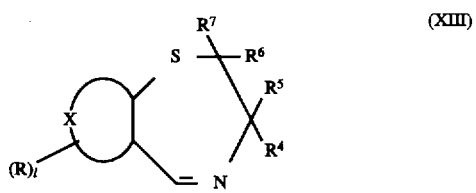

wherein 1, R, $R^4$ to $R^7$ and X are as hereinbefore defined, with, for example, an organometallic compound, such as $R^2Li$, $R^2Cu$, $R^2Zn$, or $R^2MgBr$ wherein $R^2$ is as hereinbefore defined.

Compounds of formula (XIII) can be prepared by dehydrogenating the corresponding compound of formula (XIV)

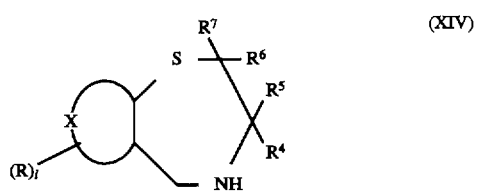

wherein 1, R, $R^4$ to $R^7$ and X are as hereinbefore defined, using, for example, an oxidising agent, such as 2,3-dichloro-5,6-dicyano-1,4-benzoquinone (DDQ), in a suitable solvent, such as toluene, or preferably $KM_nO_4$ in a suitable solvent, such as t-butanol/$H_2O$.

Alternatively, compounds of formula (XIII) can be prepared by reacting a compound of formula (IV) wherein $R^2$ is hydrogen with a compound of formula (V) or (Va).

Compounds of formula (XIV) can be prepared by reducing the amide carbonyl group of the corresponding compound of formula (XV)

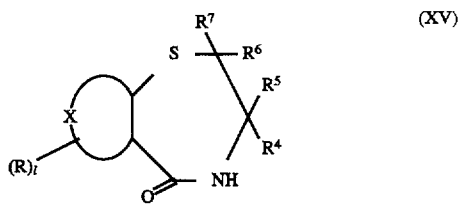

wherein 1, R, $R^4$ to $R^7$ and X are as hereinbefore defined, using, for example, lithium aluminium hydride.

Compounds of formula (XV) can be prepared by reacting a compound of formula (XVI)

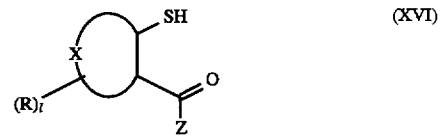

wherein 1, R and X are as hereinbefore defined and Z is $C_{1-4}$ alkoxy, for example, methoxy, with a compound of formula (V) or (Va) wherein $R^4$ to $R^7$ are as hereinbefore defined.

The compound of formula (XVI) wherein X is benzo can be prepared from a suitably $(R)_1$, substituted 2,2-dithiosalicylic acid or when 1=o, from the commercially available 2,2'-dithiosalicyclic acid by methods known to those skilled in the art. Compounds of formula (XVI) wherein 1 is not 0 can be obtained commercially or prepared by methods known to those skilled in the art or obtainable from the chemical literature.

Alternatively compounds of formula (I) wherein n=o and $R^3$ is hydrogen can be prepared by cyclising a compound of formula (XXIX)

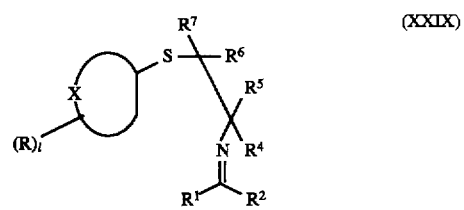

wherein 1, X, $R^1$, $R^2$ and $R^4$ to $R^7$ are as hereinbefore defined by reaction with a non-nucleophillic base such as LDA, which can then be reacted with oxone to give compounds of formula (I) wherein n=2.

Compounds of formula (XXIX) can be prepared from compounds of formula (XXX)

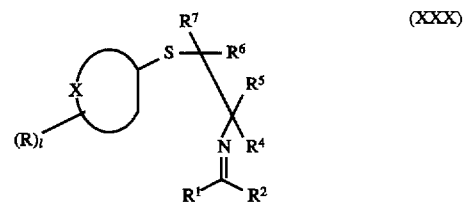

wherein 1, X, and $R^4$ to $R^7$ are as hereinbefore defined, by reaction with $R^2CHO$ wherein $R^2$ is as hereinbefore defined.

Compounds of formula (XXX) can be prepared by reaction of compound of formula (V) with compounds of formula (VI).

Compounds of formula (I) can also be prepared starting from compounds of formula (XXI)

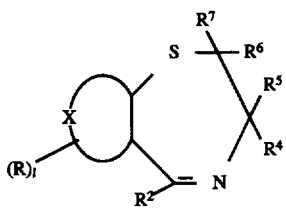

(XXI)

wherein X, 1, R, R² and R⁵ to R⁷ are as hereinbefore defined, by steps will known in the art.

Compounds of formula (XXI) can be prepared by following methods described herein which methods will be obvious to one skilled in the art.

Compounds of formula XXI can also be prepared by reaction of compounds of formula (II) wherein R⁴=CH₂OH by oxidation of the alcohol with, for example, SO₃ pyridine in Et₃N/DMSO.

Compounds of formula (I) wherein R³=OH, $C_{1-6}$ alkoxy or $—OC_{1-6}$ acyl can be prepared from compounds of formula (I) wherein R³ is hydrogen by oxidation of the nitrogen with, for example, oxone® (potassium peroxymino sulphate) in methanol/water optionally followed by reactions known in the art.

Compounds of formula (I) wherein X=pyrrolo can be prepared from compounds of formula (XXVI)

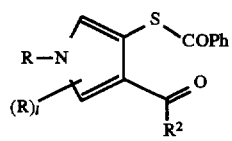

(XXVI)

wherein P is a protecting group such as tri-isopropylsilyl, R, 1 and R² are as hereinbefore defined by refluxing with a base such as NaOH followed by reaction with a compound of formula (V) or (Va) in a suitable solvent such as methanol. The resulting compound (XXVII)

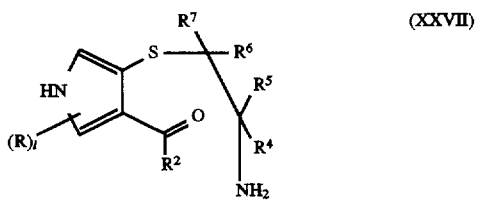

(XXVII)

wherein 1, R², R⁴, R⁵, R⁶, and R⁷ are as hereinbefore defined, is then reacted with for example lutidine/TSOH to give a compound of formula (II) wherein X=pyrrolo. These compounds can then be converted into compounds of formula (I) as previously described or by reaction with 1) BH₃/THF and 2) N-methyl morpholine-N-oxide, O₅O₄/tBuOH/THF at room temperature.

Compounds of formula (XXVI) can be prepared from compounds of formula (XXVIa)

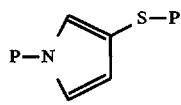

(XXVIa)

wherein P is as defined hereinbefore and can be the same or different, by reacting a compound of formula (XXVIa) with a suitable acid halide compound, such as R²COCl, wherein R² is as hereinbefore defined, by a Friedel-Crafts reacting using, for example, aluminium chloride.

The compound of formula (XXVIa) can be prepared by first reacting pyrrole with a strong base, for example n-butyllithium in an aprotic solvent such as THF, followed by N-protection with, for example TIPS-Cl (tri-isopropylsilyl chloride). The resulting N-protected pyrrole is halogenated with, for example N-Bromosuccinimide (NBS), followed by metalation with, for example t-butyllithium and reaction with sulphur (S₈). The resulting sulphur compound is further s-protected with, for example TIPS-Cl.

Compounds formula (I) wherein X=pyrridyl can be prepared from compounds of formula (XVIII) wherein X=pyrridyl by reaction with, for example, NaSH/DMSO and a compound of formula (V) or (Va).

The resulting compound of formula (III) wherein X is pyrridyl, R, 1, R², and R⁴ to R⁷ are as hereinbefore defined can be converted to a compound of formula (II) wherein X=pyrridyl as previously described. These compounds of formula (II) can then be converted to compounds of formula (I) as previously described herein.

Side-chain manipulation: Compounds of formula (I) wherein R⁴ is, for example, —CH₂CH=CHCH₃, can be hydrochlorinated using, for example, gaseous hydrogen chloride, to give the corresponding compound of formula (I) wherein R⁴ is —CH₂CHClCH₂CH₃ and then hydrolysed using, for example, basic H₂O₂, to give the corresponding compound of formula (I) wherein R⁴ is —CH₂CH(OH)CH₂CH₃. Compounds of formula (I) wherein R⁴ is —CH₂CH(OH)CH₂CH₃ can also be prepared by reducing and hydroxylating a compound of formula (II) wherein R⁴ is —CH₂CH=CHCH₃ using, for example, diborane followed by acidification and subsequent oxidation with basic H₂O₂. Compounds of formula (III) wherein R⁴ is —CH₂OH can be cyclised as described earlier to give the corresponding compound of formula (II) wherein R⁴ is, for example —CHO₂H. The latter can be oxidised using, for example, SO₃/pyridine and Et₃N in DMSO, to give the corresponding compound of formula (II) wherein R⁴ is —CHO, alkenylated using, for example, Ph₃P=CHCOCH₃ in toluene, to give the corresponding compound of formula (II) wherein R⁴ is, for example —CH=CHCOCH₃ and then (i) reduced using, for example, sodium borohydride in ethanol, to give the corresponding compound of formula (II) wherein R⁴ is —CH=CHCH(OH)CH₃ followed by reduction of the alkene, for example when n is 1 or 2 by catalytic hydrogenation using, for example, 10% Pd/C, to give the corresponding compound of formula (I) wherein R⁴ is —CH₂CH₂CH(OH)CH₃ or (ii) reduction of the alkene, for example when n is 1 or 2 by catalytic hydrogenation to give the corresponding compound of formula (I) wherein R⁴ is —CH₂CH₂COCH₃ followed by reduction of the ketone to give the corresponding compound of formula (I) wherein R⁴ is —CH₂CH₂CH(OH)CH₃. Alternatively, the compound of formula (II) wherein R³ is —CHO can be alkenylated using a wittig reagent, for example, Ph₃P⁺(CH₂)₁₋₅OH Br⁻ and n-BuLi, to give the corresponding compound of formula (II) wherein R⁴ is —CH=CH(CH₂)₀₋₄OH followed by reduction of the alkene, for example when n is 1 or 2 by catalyic hydrogenation to give the corresponding compound of formula (I) wherein R⁴ is —(CH₂ ₂₋₆OH using, for example, 10% Pd/C.

The compound of formula (II) wherein R⁴ is —CHO can be alkenylated using a wittig reagent, for example, Ph₃P⁺=CHCH₂CF₃Br⁻ followed by conversion of the alkene as described hereinbefore.

Compounds of formula (I) wherein R² is hydroxyphenyl can be prepared by debenzylation of the corresponding compound of formula (I) wherein R² is benzyloxyphenyl using, for example, 30% aqu. H₂O₂ in trifluoroacetic acid or 10% Pd/C/hydrogen.

Compounds of formula (I) wherein n=0 and R³ is not hydrogen can be prepared by N-alkylation of the corresponding compound of formula (II) with an alkyl halide, such as methyl iodide, in a polar solvent, for example, acetonitrile, prior to reduction to the compound of formula (I).

Compounds of formula (I) wherein n=1 or 2 can be prepared by oxidation of the corresponding compound of formula (I) wherein n=0 or by oxidation of the corresponding compound of formula (III) wherein n=0 prior to cyclisation and reduction to the compound of formula (I) using suitable oxidation condition, for example, in the case where n is to be 2.30% aqu. $H_2O_2$ in the presence of trifluoroacetic acid.

Individual optical isomers of compounds of formula (I) substantially free, of other optical isomers can be obtained either by chiral synthesis, for example, by the use of the appropriate chiral starting material(s), such as the aziridine (V), or by resolution of the products obtained from achiral syntheses, for example, by chiral hplc.

Optional conversion of a compound of formula (I) to a corresponding acid addition salt can be effected by reaction with a solution of the appropriate acid, for example, one of those recited earlier. Optional conversion to a corresponding base salt may be effected by reaction with a solution of the appropriate base, for example, sodium hydroxide. Optional conversion to a physiologically functional derivative, such as an ester, can be carried out by method known to those skilled in the art or obtainable from the chemical literature.

For a better understanding of the invention, the following Examples are given by way of illustration and are not to be construed in any way as limiting the scope of the invention.

SYNTHETIC EXAMPLE 1

Preparation of (+−)-trans-3-ethyl-2,3,4,5-tetrahydro-3-((2R)-2hydroxybutyl)-5-phenyl-1,4-benzothiazepine 1,1-dioxide (a) Ethyl 2-aminobutyrate hydrochloride A slurry of 2-aminobutyric acid (100 g, Aldrich) in absolute ethanol (300 ml) was stirred under nitrogen at 0° C. and thionyl chloride (120.8 g) was added dropwise. The reaction was stirred overnight at 0° C. and then gradually warmed to room temperature. The resulting white slurry was heated under reflux for 3 hours, left to cool for 10 minutes, then poured into chilled diethyl ether (600 ml), with hand stirring. The suspension was filtered and the solid product dried to give the desired product (150 g) as a white solid. $^1$H NMR consistent with proposed structure.

(b) Ethyl 2-benzylideneaminobutyrate

A solution of the product from step (a) (149.6 g), magnesium sulphate (74.3 g), and triethylamine (246 ml) in dichloromethane (1500 ml) was stirred at room temperature under nitrogen and benzaldehyde (94.9 g, Aldrich) was added dropwise. The mixture was stirred at room temperature for 3 hours then filtered. The filtrate was concentrated, triturated in diethyl ether, filtered and concentrated to yield the desired product as a yellow oil (174 g). $^1$H NMR consistent with the proposed structure.

(c) (+−)-Etheyl 2-benzylideneamino-2-ethylhex-4-enoate

A solution of the product from step (b) (159 g) in THF (100 ml) was added to a suspension of potassium hydride (64 g) in THF (350 ml) at a temperature of about 0° C. When addition was complete, the mixture was stirred at about 0° C. for 2 hours, then cooled using a dry ice/acetone bath and a solution of crotyl bromide (100 g) in THF (50 ml) added. When addition was complete, the mixture was stirred at room temperature for two days, then quenched with ethanol (60 mL) to destroy excess hydride followed by pet. ether (1500 mL) and water (25 mL). The mixture was filtered and the filtrate evaporated in vacuo to give the desired product as a dark red oil. $^1$H NMR consistent with the proposed structure.

(d) (+−)-Ethyl 2-amino-2-ethylhex-4-enoate

4N Aqueous HCl (170 mL) was added to a solution of the product from step (c) in pet. ether (1500 ml). When addition was complete, the mixture was stirred for 2 hours at about 0° C. The aqueous phase was separated, washed with pet. ether and poured into 2M $Na_2CO_3$ (200 mL) at about 0° C. The pH was adjusted to 9 by the addition of further $Na_2CO_3$ and the mixture extracted with ether. The combined extracts were dried and evaporated in vacuo to give the desired product as an oil. $^1$H NMR consistent with the proposed structure.

(e) (+−)-2-Amino-2-ethylhex-4-en-1-ol

A solution of the product from step (d) (116.7 g) in THF (100 ml) was added to a 1M solution of lithium aluminium hydride in THF (800 ml) at about 0° C. When addition was complete, the mixture was stirred overnight at room temperature, then 50% w/v aqu. NaOH (200 ml) was added. The organic phase was separated, washed with brine, dried and evaporated in vacuo. The residue was distilled to give the desired product as an oil (29.3 g). $^1$H NMR consistent with the proposed structure.

(f) (+−)-2-But-2-enyl-2-ethylaziridine

Chlorosulphonic acid (18 mL) was added to a solution of the product from step (e) (32.3 g) in acetonitrile (100 ml) at least 9° C. When addition was complete, the mixture was warmed to room temperature. The resulting crystals were filtered off, washed with acetonitrile/pet. ether, dried, taken up in a mixture of 50% w/v aqu. KOH (100 mL) and water (55 mL) and distilled over KOH to give the desired product as a colourless oil (16.1 g). $^1$H NMR consistent with the proposed structure.

(g) 2-Thiobenzophenone

A solution of N,N,N',N'-tetramethylethylenediamine (TMEDA) (104.6 g) in cyclohexane (500 ml) was cooled and 2.5M n-butyl lithium (360 ml) was added. A solution of thiophenol (50.0 g) in cyclohexane (100 ml) was added slowly to the butyl lithium solution and the reaction was stirred at room temperature overnight. Benzonitrile (46.4 g, Aldrich) in cyclohexane (100 ml) was added to give a slurry which was stirred overnight at room temperature. Water (500 ml) was added and the mixture stirred for 30 minutes, then the aqueous layer was separated and treated with solid sodium hydroxide to give pH 14. The solution was boiled for 90 minutes, cooled to room temperature and acidified to pH 1–2 with conc. HCl. The acidic solution was extracted with dichloromethane and the combined extracts dried, then concentrated to give a red oil. The oil was treated with 1N NaOH, extracted with dichloromethane and the aqueous layer separated and treated with conc. HCl to give an oil. The oil was extracted into dichloromethane and the combined extracts dried, then concentrated to give the desired product as an orange-red oil (83.4 g). $^1$H NMR consistent with proposed structure.

(h) (+−)-3-Ethyl-3-but-2-enyl-5-phenyl-2,3-dihydrobenzothiazepine

The products from steps (f) (8.0 g) and (g) (12.9 g) were taken up in 2,6-lutidine, stirred for 2 hours and conc. HCl (5 mL) was added. When addition was complete, the mixture was azeotroped overnight at 180° C., then cooled and evaporated in vacuo. The residue was taken up in 5% w/v aqu. $NaHCO_3$ and the solution extracted with ethyl acetate. The combined extracts were washed with brine, dried and evaporated in vacuo. The residue was flash chromatographed on silica gel using 80:20 hexane/ethyl acetate as eluant to give the desired product as an orange oil (18.4 g). $^1$H NMR consistent with the proposed structure.

(i) (+−)-3-((2R)-3-Hydroxybutyl)-3-ethyl-2,3,4,5-tetrahydro-5-phenyl-1,4-benzothiazepine A 1M solution of diborane in THF (31.7 mL) was added to a solution of the product from step (h) in THF (1500 mL). When addition was complete, the mixture was stirred overnight at room temperature, then 50% v/v aqu. HCl (100 mL) was added. When addition was complete, the mixture was concentrated in vacuo to remove the THF. 50% w/v aqu NaOH and ethyl acetate were added to the remaining aqueous phase and the organic phase separated, dried and evaporated in vacuo. The residue was taken up in THF (150 mL) and 3N NaOH (52 ml) followed by 30% $H_2O_2$ (17.7 g) were added. When addition was complete, the mixture was stirred at room temperature for 3.5 hours, then satd. aqu. $Na_2CO_3$ was added. The organic phase was separated, dried and evaporated in vacuo. The residue was chromatographed on silica gel using 70:30 hexane/ethyl acetate as eluant to give the desired product as an oil (1.5 g).

(j) (+−)-Trans-3-ethyl-2,3,4,5-tetrahydro-3-((2R)-2-hydroxybutyl)-5-phenyl-1,4-benzothiazepine 1,1-dioxide A solution of the product from step (i) (1.5 g) in trifluoroacetic acid (25 mL) was added to a solution of 30% $H_2O_2$ (1.4 g) in trifluoroacetic acid (5 mL). When addition was complete, the mixture was stirred overnight at room temperature, then added to deionized water (300 mL), basified with 1N NaOH and stirred for 1 hour. The resulting precipitate was filtered off and triturated with 1N NaOH for 1 hour, then filtered and dried to give the desired product as a white solid, mp 149°–151° C. (1.5 g).

Analysis: Calcd. C 66.24; H 7.36; N 3.68; S 8.40
Found: C 66.31; H 7.25; N 3.64; S 8.49

$^1$H NMR (DMSO-$d_6$), δ: 0.77–0.93 (6H, m 2x $CH_3$); 1.21–1.38 (2H, m, $CH_2$); 1.69–1.85 (3H, m, $CH_2$—NH); 2.30–2.43 (1H, m, CH); 3.59–3.69 (1H, m, OH); 3.62 (2H, q, $CH_2SO_2$); 6.26 (1H, s, CHPh); 6.57–6.63 (1H, m, ArH); 7.36–7.63 (7H, m, ArH); 8.00–8.06 (1H, m, ArH).

SYNTHETIC EXAMPLE 2

Preparation of (+−)-trans-1-(3-ethyl-2,3,4,5-tetrahydro-8-methoxy-5-phenyl-1,4-benzothiazepin-3-yl-2(R)-2-butanol S,S-dioxide (a) O-(2-benzoyl-5-methoxyphenyl) dimethylthiocarbamate Sodium hydride (8.8 g, Aldrich) was added slowly to a solution of 2-hydroxy-4-methoxybenzophenone (50.0 g, Aldrich) in 300 ml of dimethylformamide. Hexamethylphosphoramide (43.0 g) was then added dropwise and stirred at room temperature for 2 hours. Dimethylthiocarbamoyl chloride (37.0 g, Aldrich) was added and stirred overnight at 50° C. The reaction mixture was poured into deionized water (300 mL) and extracted with a petroleum ether/chloroform (1:4) mixture. The organic layer was washed with 10% sodium hydroxide, brine and concentrated to give the title product as a yellow solid (40.0 g), mp 94°–96° C. $^1$H NMR was consistent with proposed structure.

(b) S-(2-Benzoyl-5-methoxyphenyl) dimethylthiocarbamate

The product (40.0 g) from step (a) was suspended in phenyl ether (300 mL) and heated to an internal temperature of 262° C. for 30 minutes. After cooling to room temperature, the reaction mixture was chromatographed on silica using hexane, then hexanes/ethyl acetate (7:3) as eluants to afford the title product as a yellow-brown solid (30.0 g), mp 96°–98° C. $^1$H NMR was consistent with proposed structure.

(c) 2-Mercapto-4-methoxybenzophenone

Potassium hydroxide pellets (20.0 g) was slowly added to a solution of the product (28.0 g) from step (b) dissolved in 800 ml methanol/tetrahydrofuran (1:1). After refluxing for 4 hours, the reaction was cooled to room temperature, methylene chloride was added and the solution was extracted with 5% hydrochloric acid. The organic layer was dried and concentrated. Chromatography on silica using hexanes/ethyl acetate (99:1) as the eluant afforded the title product as a yellow solid (17.1 g), mp 74°–76° C. $^1$H NMR consistent with proposed structure.

(d) (+−)-3-But-2-enyl-3-ethyl-8-methoxy-5-phenyl-2,3-dihydrobenzothiazepine

This compound was prepared following the procedure of Synthetic Example 1 (h), using the product from step (c) (32.0 g) and the product from Synthetic Example 1 (f) (18.8 g), but replacing etheral HCl with p-toluenesulphonic acid (200 mg). Chromatography on silica using hexanes/EtOAc (9:1) as eluant gave the desired product as an orange oil (35.7 g). $^1$H NMR consistent with the proposed structure.

(e) (+−)-Trans-1-(3-ethyl-2,3,4,5-tetrahydro-8-methoxy-5-phenyl-1,4-benzothiazepin-3-yl)-2(R)-2-butanol This compound was prepared following the procedure of Synthetic Example 1 (i), using the product from step (d) (35.7 g). Chromatography on silica using hexanes/EtOAc (65:35) as eluant afforded the title product as an orange oil (27.7 g). $^1$H NMR consistent with the proposed structure.

(f) (+−)-Trans-1-(3-ethyl-2,3,4,5-tetrahydro-8-methoxy-5-phenyl-1,4-benzothiazepin-3-yl)-2(R)-2-butanol S,S-dioxide This compound was prepared following the procedure of Synthetic Example 1 (j), using the product from step (e) (27.7 g) to give solids which were recrystallized from acetone to give the desired product as a white solid (12.3 g), mp 201°–202° C.

Analysis: C65.48; H 7.24; N 3.47; S 7.95
Found: C 65.51; H 7.29; N 3.38; S 8.01

$^1$H NMR (DMSO-$d_6$), δ; 0.79 (3H, t, $CH_3$); 0.84 (3H, t, $CH_3$); 1.22–1.30 (2H, m, $CH_2$); 1.62–1.71 (3H, m, $CH_2$); 2.21–2.26 (1H, m, $CH_2$); 3.14 (1H, d, NH); 3.45 (2H, q, $CH_2SO_2$); 3.55–3.59 (1H, m CH); 3.78 (3H, s, $OCH_3$); 4.52 (1H, s, OH); 6.04 (1H, d, CHPh); 6.42 (1H, d, ArH); 7.02–7.05 (1H, m, ArH); 7.29–7.43 (6H, m, ArH)

SYNTHETIC EXAMPLE 3

Preparation of (+−)-trans-1-(3-ethyl-2,3,4,5-tetrahydro-8-methoxy-5-phenyl-1,4-benzothiazepin-3-yl)-3-butanol S,S-dioxide (a) (+−)-Trans-1-(3-ethyl-2,3,4,5-tetrahydro-8-methoxy-5-phenyl-1,4-benzothiazepin-3-yl-3-butanol This compound was isolated as a light yellow oil (4.7 g) as a minor product of Synthetic Example 2 (e). $^1$H NMR consistent with the proposed structure.

(b) (+−)-Trans-1-(3-ethyl-2,3,4,5-tetrahydro-8-methoxy-5-phenyl-1,4-benzothiazepin-3-yl)-3-butanol S,S-dioxide This compound was prepared following the procedure of Synthetic Example 1 (j), using the product from step (a) (3.0 g) to give a white solid (0.70 g), mp 119°–122° C.

Analysis: C 65.48; H 7.24; N 3.47; S 7.95
Found: C 65.57; H 7.31; N 3.54; S 8.02

$^1$H NMR (DMSO-$d_6$), δ: 0.78–0.98 (6H, m, $CH_3$); 1.10–1.26 (2H, m, $CH_2$); 1.40–1.50 (2H, m, $CH_2$); 1.73–1.84 (1H, m, $CH_2$); 2.02–2.14 (1H, m, $CH_2$); 2.50 (1H, d, NH); 3.39 (2H, q, $CH_2SO_2$); 3.42–3.51 (1H, m, CH); 3.80 (3H, s, $OCH_3$); 4.32 (1H, d, OH); 5.87 (1H, d, CHPh); 6.50 (1H, d, ArH); 7.06 (1H, dd, ArH); 7.28–7.48 (6H, m, ArH)

SYNTHETIC EXAMPLE 4

Preparation of (+−)-trans-1-(3-ethyl-2,3,4,5-tetrahydro-7-methoxy-5-phenyl-1,4-benzothiazepin-3-yl)-2(R)-2-butanol S,S-dioxide (a) 2-Mercapto-5-methoxybenzophenone This compound was prepared following the procedure of Synthetic Example 1 (g), using 4-methoxybenzenethiol (20.0 g, Aldrich). Chromatography on silica with hexanes/ dichloromethane (1:1) as eluant afford the title product as a yellow oil (2.9 g). $^1$H NMR consistent with the proposed structure.

(b) (+−)-Trans-1-(3-ethyl-2,3,4,5-tetrahydro-7-methoxy-5-phenyl-1,4-benzothiazepin-3-yl)-2(R)-2-butanol S,S-dioxide The title compound was prepared following the procedures of Synthetic Example 1 (h)–1 (j) using the product from step (a) to give a white solid, mp 167°–168° C.
Analysis: C, 65.48; H 7.24; N 3.47; S, 7.95
Found: C 65.38; H 7.25; N 3.44; S 8.03

$^1$H NMR (DMSO-d$_6$), δ: 0.77–0.89 (6H, m, CH$_3$); 1.21–1.31 (2H, m, CH$_2$); 1.60–1.76 (3H, m, CH$_2$); 2.20–2.33 (1H, m, CH$_2$); 3.34 (1H, d, NH); 3.34 (2H, q, CH$_2$SO$_2$); 3.57–3.63 (1H, m, CH); 3.66 (3H, s, OMe; 5.94 (1H, broad s, ArH); 6.08 (1H, d, CHPh); 7.03 (1H, dd, ArH); 7.34–7.46 (5H, m ArH); 7.92 (1H, d, ArH)

SYNTHETIC EXAMPLE 5

Preparation of (+−)-trans-1-(3-ethyl-5-(4-fluorophenyl)-2,3, 4,5-tetrahydro-7-methoxy-1,4-benzothiazepin-3-yl)-2(R)-2-butanol S,S-dioxide (a) 4'-Fluoro-2-mercapto-5-methoxybenzophenone This compound was prepared following the procedure of Synthetic Example 1 (g), using 4-methoxybenzenethiol (58.0 g, Aldrich) and 4-fluorobenzonitrile (50.0 g, Aldrich). Chromatography on silica with hexanes/dichloromethane (1:1) as eluant afforded the desired compound as an orange oil (6.11 g). $^1$H NMR consistent with the proposed structure.

(b) (+−)-Trans-1-(3-ethyl-5-(4-fluorophenyl)-2,3,4,5-tetrahydro-7-methoxy-1,4-benzothiazepin-3-yl)-2(R)-2-butanol S,S-dioxide The title compound was prepared following the procedures of Synthetic Example 1 (h)–1 (j) using the product from step (a) to give a white solid, mp 9-°–92° C.
Analysis: C 62.69; H 6.70; N 3.32 S 7.61
Found C 62.48 H 6.81 N 3.37 S 7.66

$^1$H NMR (DMSO-d$_6$), δ: 0.77–0.89 (6H, m, CH$_3$); 1.22–1.32 (2H, m, CH$_2$); 1.59–1.76 (3H, m, CH$_2$); 2.17–2.30 (1H, m, CH$_2$); 3.30 (1H, d, NH); 3.39 (2H, q, CH$_2$SO$_2$); 3.52–3.66 (1H, m, CH); 3.68 (3H, s, OCH$_3$); 5.95 (1H, d, ArH); 6.07 (1H, d, CHPh); 7.03 (1H, dd, ArH); 7.19–7.45 (4H, m, ArH); 7.93 (1H, d, ArH)

SYNTHETIC EXAMPLE 6

Preparation of (+−)-trans-1-(3-ethyl-5-(4-hydroxyphenyl)-2,3,4,5-tetrahydro-1,4-benzothiazepin-3-yl)-2(R)-2-butanol S,S-dioxide 0.5 hydrate (a) 4-Benzyloxy-2-mercaptobenzophenone This compound was prepared following the procedure of Synthetic Example 1 (g), using benzenethiol (48.2 g, Aldrich) and 4-benzyloxybenzonitrile (91.6 g) to give a tan solid (112.4 g), mp 122°–123° C. $^1$H NMR consistent with the proposed structure.

(b) (+−)-Trans-1-(3-ethyl-5-(4-hydroxyphenyl)-2,3,4,5-tetrahydro-1,4-benzothiazepin-3-yl)-2(R)-2-butanol S,S-dioxide 0.5 hydrate The title compound was prepared following the procedures of Synthetic Example 1 (h)–1 (j) but using the product from step (a) to give a white solid, mp 197°–198° C.
Analysis: C 63.28; H 7.08; N 3.51; 8.05
Found: C 63.25; H 7.00; N 3.41; S 8.04

$^1$H NMR (DMSO-d$_6$), δ: 0;77–0.85 (6H, m, CH$_3$); 1.22–1.31 (2H, m, CH$_2$); 1.61–1.69 (3H, m, CH$_2$); 2.21–2.29 (1H, m, CH$_2$); 3.19 (1H, d, NH); 3.43 (2H, q, CH$_2$SO$_2$); 3.53–3.58 (1H, m, CH); 4.53 (1H, s, OH); 6.00 (1H, d, CHPh); 6.59–6.62 (1H, m ArH); 6.76 (2H, d, ArH); 7.12 (2H, d, ArH); 7.43–7.50 (2H, m, ArH); 7.92–7.94 (1H, m ArH); 9.39 (1H, s, ArOH)

SYNTHETIC EXAMPLE 7

Preparation of (+−)-trans-3-butyl-3-ethyl-2,3,4,5-tetrahydro-5-(4-hydroxyphenyl)-1,4-benzothiazepin 1,1-dioxide hydrochloride (a) (+−)-2-Butyl-2-ethylaziridine Using ethyl iodide in place of crotyl bromide in step (c) of Synthetic Example 1, the title compound was prepared in an analogus fashion to give a colorless oil. $^1$H NMR consistent with the proposed structure.

(b) (+−)-2-(2-Amino-2-ethylhexylthio)-4'-benzyloxybenzophenone

The product from step (a) (15.0 g) was dissolved in methanol (25 ml) and the product from Synthetic Example 6 (a) (35.2 g) in methanol (250 ml) was added. The mixture was stirred at room temperature for 17 hr and then concentrated in vacuo. The residue was chromatographed on silica with EtOAc then EtOAc/MeOH (1:1) as eluants to afford the title product as an orange oil (46.3 g) $^1$H NMR consistent with the proposed structure.

(c) (+−)-2-(2-Amino-2-ethylhexylsulfonyl)-4'-benzyloxybenzophenone

This compound was prepared following the procedure of Synthetic Example 1 (j), using the product from step (b) (46.3 g). Chromatography on silica using EtOAc/MeOH (9:1) as the eluant gave the desired product as an orange oil (37.5 g). $^1$H NMR consistent with the proposed structure.

(d) (+−)-3-Ethyl-3-butyl-5-(4-benzyloxyphenyl)-2.3-dihydrobenzothiazepine 1,1-dioxide This compound was prepared following the procedure of Synthetic Example 1 (h), using the product from step (c) (37.5 g). Chromatography on silica using hexanes/EtOAc (7:3) as the eluant afforded the title product as an orange oil (24.8 g). $^1$H NMR consistent with the proposed structure.

(e) (+−)-Trans-3-butyl-3-ethyl-2,3,4,5-tetrahydro-5-(4-benzyloxyphenyl)-1,4-benzothiazepine 1,1-dioxide A 1M solution of diborane in THF (60.0 ml, Aldrich) was added to a solution of the product from step (d) (24.8 g) in THF (150 ml). The mixture was stirred overnite at room temperature, then 6N HCl (100 ml) was added. The reaction mixture was concentrated in vacuo and the residue was partitioned between NaOH and EtOAc. The organic layer was separated, dried and concentrated. Chromatography on silica using hexanes/EtOAc (85:15) as eluant gave the desired product as a white solid (7.6 g), mp 94°–95° C. $^1$H NMR consistent with the proposed structure.

(f) (+−)-Trans-3-butyl-3-ethyl-2,3,4,5-tetrahydro-5-(4-hydroxyphenyl)-1,4-benzothiazepine 1,1-dioxide hydrochloride Palladium on carbon (10%. 2 g Aldrich) was added to a solution of formic acid (2.8 g, Aldrich), sodium formate (1.0 g, Fisher) and the product from step (e) (7.0 g) in EtOH (250 ml). The reaction mixture was stirred at reflux for 5 hr. then stirred at room temperature for 17 hr. The reaction mixture was filtered, concentrated in vacuo and then dissolved in 1N NaOH. Next, 1N HCl was added til acid to litmus paper then solid NaHCO$_3$ was added to neutralize the solution. The mixture was extracted with diethyl ether, separated, dried and concentrated to give a light orange oil. Chromatography on silica using hexanes/EtOAc (7:3) as eluant afforded an oil which was treated with ethereal HCl to give the title product as a white solid (0.78 g), mp 253°–254° C.

Analysis: C 61.52; H 6.88; N 3.42; S 7.88 Found: C 61.52; H 6.93; N 3.48; S 7.90

$^1$H NMR (DMSO-d$_6$), δ: 0.80–0.91 (6H, m, 2×CH$_3$); 1.25–2.02 (8H, broad m, 4×CH$_2$); 2.50 (1H, broad s, NH); 3.48 (1H, broad s, CH$_2$SO$_2$); 4.10 (1H, broad s, CH$_2$SO$_2$); 6.14 (1H, broad s, CHPh); 6.96 (4H, d, ArH); 7.36 (2H, d, ArH); 7.64 (2H, broad s, ArH); 8.05–8.08 (1H, m, ArH); 10.0+11.3 (1H, broad s, NH$^{30}$)

SYNTHETIC EXAMPLE 8

Preparation of (+−)-cis-3-ethyl-2,3,4,5-tetrahydro-3-(4-hydroxybutyl)-5-phenyl-1,4-benzothiazepine 1,1-dioxide hydrochloride (a) (+−)-Ethyl-4-(hydroxymethyl)-2-oxazolidinone Sodium methoxide (2.2 g, Aldrich) was added to a solution of 2-amino-2-ethyl-1,3-propanediol (100.0 g, Aldrich) and diethyl carbonate (169.0 g, Aldrich) This solution was refluxed in a Dean Stark apparatus until no more EtOH was collected. The reaction mixture was cooled, added acetone (200 ml) and allowed to stand overnite at room temperature. The resulting suspension was filtered to give 81.0 g of the desired product as a beige solid. $^1$H NMR consistent with the proposed structure.

(b) (+−)-4-Ethyl-4-[(tosyloxy)methyl]-2-oxazolidinone

Tosyl chloride (142.2 g, Aldrich) was added to an ice-chilled solution of the product from step (a) (102.7 g) dissolved in pyridine (175 ml, Aldrich). The reaction mixture was stirred at ice bath temperature for six hours, then allowed to come to room temperature. The heterogeneous mixture was added to 1500 ml of a solution of brine and 1N HCl, stirred until solids appeared, filtered and washed with diethyl ether to give 194.6 g of a beige solid as the title product. $^1$H NMR consistent with the proposed structure.

(c) (+−)-4-(((2-Benzoylphenyl)thio)methyl)-4-ethyl-2-oxazolidinone

2-Thiobenzophenone (125.3 g, Synthetic Example 1 (g)) in 150 ml of DMF was added slowly to sodium hydride (60%, 23.4 g, Aldrich) in 175 ml of DMF. After complete addition, the product from step (b) (175.1 g), in 200 ml of DMF, was added, in a steady stream, to the reaction mixture. The reaction was stirred at 60° C. for 3 hr, cooled and added to 3 L of brine to give solids. The reaction mixture was filtered and the solids were slurried in 250 ml of 95% EtOH and filtered to give the desired product as a beige solid (168.8 g), mp 103°–104° C. $^1$H NMR consistent with the proposed structure.

(d) (+−)-2,3-Dihydro-3-ethyl-5-phenyl-1,4-benzothiazepine-3-methanol

The product from step (c) (168.8 g) was dissolved in 1200 ml EtOH/water (2:1) and 128.8 g of KOH was added and refluxed for 24 hrs. The reaction mixture was cooled and concentrated in vacuo then ethyl acetate and deionized water were added. The organic layer was separated and concentrated in vacuo to give 155.2 g of a red-orange oil. Chromatography on silica using hexanes/EtOAc (1:1) as eluant afforded the title product as a light orange oil (55.7 g). $^1$H NMR consistent with the proposed structure.

(e) (+−)-3-Ethyl-2,3-dihydro-5-phenyl-1,4-benzothiazepine-3-carbaldehyde

Triethyl amine (56.7 g, Aldrich) was added to a solution of the product from step (d) (55.7 g) dissolved in 140 ml of DMSO. The reaction mixture was chilled to 8°–10° C. and sulfur trioxide pyridine complex (89.3 g, Aldrich) in 200 ml of DMSO was added over a period of 16 minutes. The reaction mixture was stirred for 5 hr, allowing bath temperature to come to room temperature, then added to 3 L of brine. This mixture was extracted with ethyl acetate which was separated, dried and concentrated to give 56.0 g of a red oil. Hexane (200 ml) was added, allowed to stir until solids formed, and then filtered to give the desired product as a tan solid (43.1 g) mp 98°–100° C. $^1$H NMR consistent with the proposed structure.

(f) 2-(3-Bromopropoxy)-2H-tetrahydropyran

This compound was prepared by mixing 3-bromo-1-propanol (25.0 g, Aldrich) and 3,4-dihydro-2H-pyran (22.7 g, Aldrich) in dichloromethane (600 ml) and stirring for four hours at room temperature. Brine was added to the reaction mixture and the organic layer was separated, dried and concentrated to get a liquid. Chromatography on silica using hexanes/EtOAc (4:1) as eluant afforded the title product as a colorless liquid (37.9 g). $^1$H NMR consistent with the proposed structure.

(g) 3-Hydroxypropyltriphenylphosphonium bromide

The product from step (f) (47.8 g) was added to a mixture of triphenyl phosphine (56.2 g, Aldrich) and a few crystals of iodine in 1 L of toluene. The reaction mixture was gently refluxed for a period of 62 hr, cooled and filtered to get a beige solid (55.2 g), mp 227°–228° C. $^1$H NMR consistent with the proposed structure.

(h) (+−)-4-(3-Ethyl-2,3-dihydro-1,4-benzothiazepin-3-yl)-3-butenol

A 2.5M solution of n-butyl lithium (20.0 ml, Aldrich) was added to an ice-chilled solution of the product from step (g) (9.6 g) in THF (150 ml). After complete addition, the ice bath was removed and the product from step (e) (6.0 g) in THF (20 ml) was added. The mixture was stirred at room temperature for 17 hr and then a saturated solution of NH$_4$Cl (120 ml) was added. The organic layer was separated, dried and concentrated in vacuo. Chromatography on silica using hexanes/EtOAc (85:15) as eluant gave the title product as an orange oil (4.6 g). $^1$H NMR consistent with the proposed structure.

(i) (+−)-4-(3-Ethyl-2,3-dihydro-1,4-benzothiazepin-3-yl)-3-butenol 1,1-dioxide

Alumina (12 g, activity grade I, type WB-2, basic, Sigma) was added in portions to Oxone (potassium peroxymonosulfate) (22.9 g, Aldrich) and the product from step (h) (4.2 g) in 100 ml CH$_2$Cl$_2$. The reaction mixture was stirred at gentle reflux for 3 hr then at room temperature for 17 hr. The mixture was filtered and the filtrate was washed with 5% NaHCO$_3$. The organic layer was separated, dried and concentrated to give an orange oil (3.4 g). $^1$H NMR consistent with the proposed structure.

(j) (+−)-Cis-3-Ethyl-2,3,4,5-tetrahydro-3-(4-hydroxybutyl)-5-phenyl-1,4-benzothiazepine 1,1-dioxide hydrochloride The product from step (i) 3.4 g was dissolved in 60 ml of EtOAc and 1.7 g of 10% Pd/C (Aldrich) was added, then placed on a Parr hydrogenator for 10 days. The reaction mixture was filtered and concentrated in vacuo to give an oil. Chromatography on silica using hexane/EtOAc (3:2) as eluant gave a slightly yellow oil which was treated with ethereal HCl to give the title product as a white solid (0.50 g), mp 193°–194° C.

Analysis: Calcd. C 61.52; H 6.88; N 3,42; S 7.82 Found: C 61.50; H 6.86; N 3.43; S 7.88

$^1$H NMR of the free base (DMSO-d$_6$); δ: 0.80 (3H, t, CH$_3$); 1.10–1.55 (6H, m, 3×CH$_2$); 1.75–1.85 (1H, m, CH$_2$); 1.96–2.07 (1H, m, CH$_2$); 2.60 (1H, d, NH); 3.20–3.35 (2H, m, CH$_2$); 3.40 (2H, q, CH$_2$SO$_2$); 4.27 (1H, t, OH); 5.94 (1H, d, CHPh); 6.42–6.50 (1H, m, ArH); 7.30–7.43 (7H, m, ArH), 7.93–7.99 (1H, m, ArH)

SYNTHETIC EXAMPLE 9

Preparation of (+−)-trans-3-ethyl-2,3,4,5-tetrahydro-3-(4-hydroxybutyl)-5-phenyl-1,4-benzothiazepine 1,1-dioxide This product was isolated from Synthetic Example 8 (j) as an orange oil which upon stirring in EtOH/water afforded a white solid (0.070 g), mp 136°–139° C.

Analysis: C 67.53; H 7.29; N, 3.75; S 8.59 Found: C 67.93; H 7.60; N 3.58; S 8.30

$^1$H NMR (DMSO-d$_6$), δ: 0.66 (3H, t, CH$_3$); 1.20–1.44 (6H, m, 3×CH$_2$); 1.70–1.78 (1H, m, CH$_2$); 2.11–2.18 (1H, m, CH$_2$); 2.63 (1H, d, NH); 3.36–3.40 (2H, m, CH$_2$); 3.39 (2H, q, CH$_2$SO$_2$); 4.33 (1H, t, OH); 5.94 (1H, d, CHPh); 6.55–6.58 (1H, m, ArH); 7.29–7.47 (7H, m, ArH); 7.95–7.98 (1H, m, ArH)

SYNTHETIC EXAMPLE 10

Preparation of (+–)-trans-3-butyl-3-ethyl-2,3,4,5-tetrahydro-7-hydroxy-5-phenyl-1,4-benzothiazepine 1,1-dioxide (a) Bis(4-isopropyloxyphenyl)disulfide A mixture of bis(4-hydroxyphenyl)disulfide (88.0 g, Parish), potassium carbonate (194.0 g), 2-bromopropane (297.6 g) and anhydrous dimethylformamide (1500 ml) were stirred at room temperature for 2 days. Inorganics were filtered and the filtrate was concentrated. The residue was partitioned between ethyl acetate (600 ml) and brine (300 ml). The organic layer was separated, washed with brine, dried and concentrated to give the title product as a beige solid (112.4 g), mp 62°–64° C. $^1$H NMR consistent with the proposed structure.

(b) 4-(Isopropyloxy)benzenethiol

Ethanol (225 ml) and the product from step (a) (33.8 g) were mixed under N$_2$ and sodium borohydride (7.6 g) was added in several portions. The mixture was refluxed for 2 hours, conc. HCl was added to bring the pH to 2 and the mixture concentrated in vacuo. The residue was partitioned between dichloromethane (200 ml) and water (200 ml). The organic layer was separated, washed with brine, dried and concentrated to give the title product as a yellow oil (30.5 g). $^1$H NMR consistent with the proposed structure.

(c) 2-Mercapto-5-(isopropyloxy)benzophenone

This compound was prepared following the procedure of Synthetic Example 1 (g), using the product from step (b) (39.6 g). Chromatography on silica with hexanes/dichloromethane (2;1) as eluant afforded the title product as an orange oil (24.0 g). $^1$H NMR consistent with the proposed structure.

(d) (+–)-Butyl-3-ethyl-7-(isopropyloxy)-5-phenyl-2,3-dihydrobenzothiazepine

This compound was prepared following the procedure of Synthetic Example 1 (h), using the product from step (c) (24.0 g). Chromatography on silica with hexanes/toluene (1:1) as eluant afforded the title product as a yellow oil (20.8 g). $^1$H NMR consistent with the proposed structure.

(e) (+–)-Trans-3-butyl-3-ethyl-2,3,4,5-tetrahydro-7(isopropyloxy)-5-phenyl-1,4-benzothiazepine This compound was prepared following the procedure of Synthetic Example 1 (i), using the product from step (d) (20.8 g). Gradient chromatography on silica with hexanes/toluene (1:1), toluene and ethyl acetate as the eluants afforded the title product as a yellow oil (8.2 g). $^1$H NMR consistent with the proposed structure.

(f) (+–)-Trans-3-butyl-3-ethyl-2,3,4,5-tetrahydro-7-(isopropyloxy)-5-phenyl-1,4-benzothiazepine 1,1 dioxide This compound was prepared following the procedure of Synthetic Example 1 (j), using the product from step (e) (8.2 g). Chromatography on silica with hexanes/ethyl acetate (6:1) as eluant afforded the title product as a white solid (1.9 g). $^1$H NMR consistent with the proposed structure.

(g) (+–)-Trans-3-butyl-3-ethyl-2,3,4,5-tetrahydro-7-hydroxy-5-phenyl-1,4-benzothiazepine 1,1 dioxide The product from step (f) (1.4 g) was dissolved in dichloromethane (108 ml) under N$_2$ and cooled to –10° C. A 1M solution of boron trichloride in dichloromethane (92 ml, Aldrich) was added dropwise. The reaction was stirred at –10° C. for 30 minutes. Water (68 ml) was added dropwise and the mixture was stirred at room temperature for 30 minutes. Saturated aqueous sodium bicarbonate (200 ml) and dichloromethane (200 ml) were added. The organic layer was separated, dried and concentrated. Chromatography on silica with hexanes/ethyl acetate (2:1) as eluant afforded the title product as an off-white solid (0.9 g) mp 80°–82° C.

Analysis: Calcd. C 67.53; H 7.35; N 3.69; S 8.44 Found: C 67.34; H 7.28; N 3.70; S 8.68

$^1$H NMR (DMSO-d$_6$), δ: 0.72 –0.85 (6H, m, CH$_3$); 1.07–1.23 (4H, m, CH$_2$); 1.40–1.48 (2H, m, CH$_2$); 1.60–1.82 (1H, m, CH$_2$); 2.00–2.20 (1H, m, CH$_2$); 2.58 (1H, d, NH); 3.27 (2H, 1, CH$_2$SO$_2$); 5.92 (1H, d, CHPh); 6.02 (1H, d, ArH); 6.65 (1H, dd, ArH); 7.41 (5H, s, ArH); 7.80 (1H, d, ArH); 10.27 (1H, s, OH).

SYNTHETIC EXAMPLE 11

Preparation of (+–)-trans-1-(3-ethyl-2,3,4,5-tetrahydro-5-phenyl-1,4-benzothiazepin-3-yl)-4,4,4-trifluoro-(2S)-2-butanol-S,S-dioxide a) (3,3,3-Trifluoropropyl)triphenylphosphonium iodide A solution of triphenylphosphine (Aldrich, 11.7 g) and 3,3,3-trifluoropropyl iodid (Lancaster, 10 g) was vigorously refluxed in xylenes (75 mL) for 2 days. The solid which formed was filtered and washed with xylenes then air dried to yield a white solid (16.6 g). $^1$H NMR and elemental analysis are consistent with the proposed structure.

b) (+–)-(Z)-3-Ethyl-2,3-dihydro-5-phenyl-3-(4,4,4-trifluoro-1-butenyl)-1,4-benzothiazepine The product from step (a) (16.5 g) was slurried in tetrahydrofuran (THF) (250 mL) then cooled with a dry-ice/acetone bath. n-Butyl lithium (Aldrich, 2.5M, 22.0 mL) was added dropwise slowly. When the addition was complete, the bath was removed and the mixture allowed to warm to –30°. The reaction was cooled with a dry-ice/acetone bath and the aldehyde from Synthetic Example 8 (e)(11.1 g) in THF (50 mL) was added by cannula. The solution was allowed to warm to room temperature overnight. The reaction was diluted with ethyl ether, filtered through Celite™, and evaporated to crude solids. Crystallization from petroleum ether/ethyl ether/hexanes yielded a crop (1.9 g). The remaining material was chromatographed on silica gel with a suction column using 4% ethyl acetate/petroleum ether. The appropriate fractions were combined and evaporated to give a second crop of the desired product as a solid (8.47 g combined). $^1$H NMR and elemental analysis are consistent with the proposed structure.

c) (+–)-Trans-1-(3-ethyl-2,3,4,5-tetrahydro-5-phenyl-1,4-benzothiazepin-3-yl)-4,4,4-trifluoro-(2S)-2-butanol The product from step (b) (8.3 g) was dissolved in THF (60 mL). Borane-THF (Aldrich 1M/THF, 22 mL) was added dropwise and the solution was stirred at room temperature overnight. Aqueous hydrochloric acid (HCl) (6N, 20 mL) was added dropwise followed by evaporation of the solvent under reduced pressure. The yellow residue was treated with excess aqueous sodium hydroxide (NaOH) (45 mL/1N) and extracted into ethyl acetate. The solvent was evaporated to an oil which was dissolved in THF and then treated with aqueous NaOH (22 mL/5N) and hydrogen peroxide (11 mL/aqueous 30%). This mixture was stirred overnight at room temperature with vigorous stirring. The reaction was diluted with ethyl acetate and the organic layer separated, washed with a dilute solution of sodium bisulfite, and evaporated to a crude solid. The solid as chromatographed on silica gel with a suction column using 4–20% ethyl acetate/petroleum ether. The appropriate fractions were combined and evaporated to give the desired product as a solid (1.3 g). Recovered starting material (3.7 g) was treated with borane following the same procedure and chromatographed to give a second crop of the desired product as a solid (1.0 g). $^1$H NMR consistent with the proposed structure.

d) (+—)-Trans-1-(3-ethyl-2,3,4,5-tetrahydro-5-phenyl-1,4-benzothiazepin-3-yl)-4,4,4-trifluoro-(2S)-2-butanol-S,S-dioxide The compound was prepared following the procedure from Synthetic Example 1 (j), but using the product from step (c) (1.0 g). The crude solids were crystallized from acetone/hexanes, filtered and dried to give the desired product, mp 164°–168° C. (0.4 g).

Analysis: Calcd: C 59.00; :H 5.66; N 3.28; S 7.50; Found: C 59.09; H 5.65; N 3.34; S 7.57

$^1$H NMR (DMSO-d$_6$), δ: 0.88 (3H, t, CH$_3$); 1.75 (3H, m); 2.10 (0.7H, s); 2.29 (3H, m); 3.21 (1H, d); 3.38 (1H, d); 3.80 (1H, d); 4.07 (1H, br m, CH(OH)); 5.03 (1H, s, OH); 6.15 (d, 1H); 6.54 (m, 1H); 7.43 (m, 7H, ArH); 7.98 (m, 1H).

SYNTHETIC EXAMPLE 12

Preparation of (+—)-trans-1-(3-ethyl-2,3,4,5-tetrahydro-7-methoxy-5-phenyl-1,4-benzothiazepin-3-yl)-4,4,4-trifluoro-(2S)-2-butanol-S,S-dioxide a) (Z)-3-Ethyl-2,3-dihydro-7-methoxy-5-phenyl-3-(4,4,4-trifluoro-1-butenyl)-1,4-benzothiazepine The product was prepared following the procedures from Synthetic Example 8 (a)–(e) and Synthetic Example 11 (a)–(b) but using 2-(2-phenyl-1,3-dioxolan-2-yl)-4-methoxythiophenol (Rieke Metals). The crude solid was chromatographed on silica gel with a suction column using 5% ethyl acetate/petroleum ether to give the desired product as a solid (14.0 g). $^1$H NMR consistent with the proposed structure.

b) 1-(3-Ethyl-7-methoxy-5-phenyl-2,3-dihydrobenzothiazepine)-4,4,4-trifluoro-2-butanol The product from step (a) (14.0 g) was dissolved into tetrahydrofuran (THF) (156 mL). Borane-THF (Aldrich, 1M/THF, 39 mL) was added dropwise to the warm solution. The solution was refluxed for 3 hours, cooled and carefully quenched with excess aqueous sodium hydroxide (35 mL/5N). The solution was then treated with hydrogen peroxide (10 mL/aqueous 30%), warmed to 60° C. for 1 hour, and cooled. The organic layer was separated, washed with dilute aqueous sodium bisulfite and brine, dried over sodium sulfate, and evaporated to an oil (13.5 g) which was primarily one spot by thin layer chromatography. This oil was used without further purification.

c) (+—)-Trans-1-(3-ethyl-2,3,4,5-tetrahydro-7-methoxy-5-phenyl-1,4-benzothiazepin-3-yl)-4,4,4-trifluoro-2-butanol The product from step (b) (13.5 g) was dissolved in THF (75 mL) and borane.THF (Aldrich, 40 mL/1M) was added dropwise. The reaction was refluxed for 1 hour, cooled, and ethereal hydrochloric acid (Aldrich, 40 mL/1M) was added. The reaction was heated at reflux for 6 hours, cooled, boron trifluoride etherate was added and heated back to reflux. After cooling the reaction was poured into a large excess of aqueous sodium bicarbonate, extracted with ethyl acetate, washed with brine, dried over sodium sulfate, and evaporated to a crude oil. The oil was chromatographed on silica gel with a suction column using 0–15% ethyl acetate/petroleum ether as eluant to give the desired product as a solid (2.4 g). $^1$H NMR consistent with the proposed structure.

d) (+—)-Trans-1-(3-ethyl-2,3,4,5-tetrahydro-7-methoxy-5-phenyl-1,4-benzothiazepin-3-yl)-4,4,4-trifluoro-2-butanol-S,S-dioxide The product was prepared following the procedure from Synthetic Example 1 (j) but using the product from step (c) to give a crude solid which was crystallized from ethyl ether/hexanes to give a solid, mp 168°–170° C. (0.75 g). $^{13}$C NMR consistent with the proposed structure.

Analysis: Calcd: C 57.76; H 5.73; N 3.06; S 7.01; Found: C 57.88; H 5.77; N 3.08; S 7.00

$^1$H NMR (DMSO-d$_6$), δ: 0.87 (3H, t, CH$_3$); 1.68 (2H, m, CH$_2$); 1.80 (1H, d); 2.30 (2H, m, CH$_2$); 2.41 (1H, dd); 3.11 (1H, d); 3.67 (3H, s, OCH$_3$); 3.71 (1H, d); 4.06 (1H, m); 5.00 (1H, d, OH); 5.95 (1H, d, ArH); 6.09 (1H, d, CHPh); 7.04 (1H, dd, ArH); 7.31–7.46 (5H, m, ArH); 7.93 (1H, d, ArH).

Each of the following compounds of formula (I) was prepared by a method analogous to one of the synthetic routes described above. In all cases $^1$H NMR and elemental analysis were consistent with the proposed structure.

SYNTHETIC EXAMPLES 13–57

13) (+—)-Trans-2,3,4,5-Tetrahydro-3-methyl-5-phenyl-1,4-benzothiazepine-3-methanol 1,1-dioxide. mp 79°–80° C.;

14) (+—)-Cis-2,3,4,5-Tetrahydro-3-methyl-5-phenyl-1,4-benzothiazepine-3-methanol 1,1-dioxide hydrochloride 0.25 hydrate mp 222°–224° C.;

15) (+—)-Trans-4-(3-Butyl-3-ethyl-2,3,4,5-tetrahydro-1,4-benzothiazepin-5-yl)phenol hydrochloride. mp 234°–235° C. (dec);

16) (+—)-Trans-5-(4-Benzyloxyphenyl)-3-ethyl-2,3,4,5-tetrahydro-1,4-benzothiazepine-3-methanol, mp 138°–143° C.;

17) (+—)-Trans-3-Ethyl-2,3,4,5-tetrahydro-5-phenyl-1,4-benzothiapzepine-3-methanol 1,1-dioxide. mp 134°–137° C.;

18) (+—)-Trans-3-Ethyl-2,3,4,5-tetrahydro-3-(3-hydroxybutyl)-5-phenyl-1,4-benzothiazepine 1,1-dioxide, mp 151°–155° C.;

19) (+—)-Cis-3-Ethyl-2,3,4,5-tetrahydro-3-butyl-4-hydroxy-5-(3-pyridyl)-1,4-benzothiazepine 1,1-dioxide, mp 202°–205° C.;

20) (+—)-Cis-4-(3-Butyl-3-ethyl-2,3,4,5-tetrahydro-1,4-benzothiazepin-5-yl)phenol hydrochloride, mp 236°–237° C. (dec.);

21) (+—)-Cis-3-Butyl-3-ethyl-2,3,4,5-tetrahydro-5-(4-hydroxyphenyl)-1,4-benzothiazepine 1,1-dioxide, mp 163°–165° C.;

22) (+—)-Cis-3-Ethyl-2,3,4,5-tetrahydro-3-(3-hydroxybutyl))- 5-phenyl-1,4-benzothiazepine 1,1-dioxide hydrochloride. mp 206°–209° C.;

23) (+—)-Trans-3-Ethyl-2,3,4,5-tetrahydro-3-(2(R)-2-hydroxybutyl)-5-(4-hydroxyphenyl)-1,4-benzothiazepine 1,1-dioxide, mp 197°–198° C.;

24) (+—)-Trans-3-Ethyl-2,3,4,5-tetrahydro-2-(2(S)-2-hydroxybutyl)-5-(4-hydroxyphenyl)-1,4-benzothiazepine 1,1-dioxide. mp 178°–179° C.;

25) (+—)-Trans-3-Ethyl-2,3,4,5-tetrahydro-5-phenyl-1,4-benzothiazepine-3-methanol, mp 104°–106° C.;

26) (+—)-Cis-5-(4-Benzyloxyphenyl)-3-ethyl-2,3,4,5-tetrahydro-1,4-benzothiazepine-3-methanol, mp 123°–128° C.;

27) (+—)-Trans-1-(3-Ethyl-5-(4-fluorophenyl)-2,3,4,5-tetrahydro-1,4-benzothiazepin-3-yl)-2(R)-2-butanol S,S-dioxide, mp 130°–132° C.;

28) (+—)-Trans-1-(3-Ethyl-2,3,4,5-tetrahydro-5-phenyl-1,4-benzothiazepin-3-yl)-4,4,4-trifluoro-2(R)-2-butanol S,S-dioxide, mp 140°–145° C.;

29) (+−)-Trans-1-(3-Ethyl-2,3,4,5-tetrahydro-5-phenyl-1,4-benzothiazepin-3-yl)-4-fluoro-2-(RS)-2-butanol S,S-dioxide 0.50 hydrate, mp 130°–147° C.;

30) (+−)-Trans-1-(3-Ethyl-2,3,4,5-tetrahydro-5-phenyl-1,4-benzothiazepin-3-yl)-4,4,4-trifluoro-2(S)-2-butanol S,oxide, mp 159°–161° C.;

31) (+−)-Trans-1-(3-Ethyl-2,3,4,5-tetrahydro-7-methoxy-5-phenyl-1,4-benzothiazepin-3-yl)-4,4,4-trifluoro-2(S)-2-butanol S,S-dioxide, mp 168°–170° C.;

32) (+−)-Trans-1-(3-Ethyl-2,3,4,5-tetrahydro-8-methoxy-5-phenyl-1,4-benzothiazepin-3-yl)-4,4,4-trifluoro-2(S)-2-butanol S,S-dioxide, mp 175°–179° C.;

33) (+−)-Trans-1-(3-ethyl-2,3,4,5-tetrahydro-7,8-dimethoxy-5-phenyl-1,4-benzothiazepin-3-yl-2(R)-2-butanol S,S-dioxide, mp 156°–157° C.;

34) (+−)-Trans-1-(3-Ethyl-2,3,4,5-tetrahydro-7,8-dimethoxy-5-phenyl-1,4-benzothiazepin-3-yl)-4,4,4-trifluoro-2-butanol S,S-dioxide;

35) (+−)-Trans-1-(3-Ethyl-2,3,4,5-tetrahydro-8-methoxy-5-phenyl-1,4-benzothiazepin-3-yl)-3,3,4,4,4-pentafluoro-2-butanol S,S-dioxide;

36) (+−)-Trans-1-(3-Ethyl-2,3,4,5-tetrahydro-7,8-dimethoxy-5-phenyl-1,4-benzothiazepin-3-yl)-3,3,4,4,4-pentafluoro-2-butanol S,S-dioxide;

37) (+−)-Trans-3-((3-ethyl-2,3,4,5-tetrahydro-5-phenyl-3-(4,4,4-trifluoro-2-hydroxybutyl)-1,4-benzothiazepin-7-yl)oxy)propanesulfonic acid 1,1-dioxide;

38) (+−)-Trans-3-((3-ethyl-2,3,4,5-tetrahydro-5-phenyl-3-(4,4,4-trifluoro-2-hydroxybutyl)-1,4-benzothiazepin-8-yl)oxy)propanesulfonic acid 1,1-dioxide;

39) (+−)-Trans-3-((3-ethyl-2,3,4,5-tetrahydro-3-(2-hydroxybutyl)-5-phenyl-1,4-benzothiazepin-7-yl)oxy)ethyltrimethylammonium iodide 1,1-dioxide;

40) (+−)-Trans-3-((3-ethyl-2,3,4,5-tetrahydro-3-(2-hydroxybutyl)-5-phenyl-1,4-benzothiazepin-8-yl)oxy)ethyltrimethylammonium iodide 1,1-dioxide;

41) (+−)-Trans-1-(3-Ethyl-2,3,4,5-tetrahydro-7,8-diethoxy-5-phenyl-1,4-benzothiazepin-3-yl)-4,4,4-trifluoro-2-butanol S,S-dioxide;

42) (+−)-Trans-3-((3-ethyl-2,3,4,5-tetrahydro-5-phenyl-3(4,4,4-trifluoro-2-hydroxybutyl)-1,4-benzothiazepin-7-yl)oxy)ethyltrimethylammonium iodide 1,1-dioxide 43) (+−)-Trans-3-((3-ethyl-2,3,4,5-tetrahydro-5-phenyl-3(4,4,4-trifluoro-2-hydroxybutyl)-1,4-benzothiazepin-8-yl)oxy)ethyltrimethylammonium iodide 1,1-dioxide;

44) (+−)-Trans-3-((3-ethyl-2,3,4,5-tetrahydro-3-(2-hydroxybutyl)-5-phenyl-1,4-benzothiazepin-8-yl)oxy)propanesulfonic acid 1,1-dioxide;

45) (+−)-Trans-3-((3-ethyl-2,3,4,5-tetrahydro-3-(2-hydroxybutyl)-5-phenyl-1,4-benzothiazepin-7-yl)oxy)propanesulfonic acid 1,1-dioxide;

46) (+−)-Trans-1-(3-ethyl-2,3,4,5-tetrahydro-7,8-diethoxy-5-phenyl-1,4-benzothiazepin-3-yl)-2-butanol S,S-dioxide;

47) (+−)-Trans-1-(3-(2,2,2-trifluoroethyl)-2,3,4,5-tetrahydro-7,8-dimethoxy-5-phenyl-1,4-benzothiazepin-3-yl)-4,4,4-trifluoro-2-butanol S,S-dioxide;

48) (+−)-Trans-1-(3-(2,2,2-trifluoroethyl)-2,3,4,5-tetrahydro-8-methoxy-5-phenyl-1,4-benzothiazepin-3-yl)-4,4,4-trifluoro-2-butanol S,S-dioxide;

49) (+−)-Trans-1-(3-Ethyl-2,3,4,5-tetrahydro-9-methoxy-5-phenyl-1,4-benzothiazepin-3-yl)-4,4,4-trifluoro-2-butanol S,S-dioxide;

50) (+−)-Trans-1-(3-ethyl-2,3,4,5-tetrahydro-9-methoxy-5-phenyl-1,4-benzothiazepin-3-yl)-2-butanol S,S-dioxide;

51) (+−)-Trans-1-(3-Ethyl-2,3,4,5-tetrahydro-7,8-dihydroxy-5-phenyl-1,4-benzothiazepin-3-yl)-4,4,4-trifluoro-2-butanol S,S-dioxide;

52) (+−)-Trans-1-(3-ethyl-2,3,4,5-tetrahydro-8-methoxy-5-phenyl-1,4-benzothiazepin-3-yl)-1-butanol S,S-dioxide;

53) (+−)-Trans-1-(3-ethyl-2,3,4,5-tetrahydro-7,8-dimethoxy-5-phenyl-1,4-benzothiazepin-3-yl)-1-butanol S,S-dioxide;

54) (+−)-Trans-1-(3-Ethyl-2,3,4,5-tetrahydro-7,8-dihydroxy-5-phenyl-1,4-benzothiazepin-3-yl)-2-butanol S,S-dioxide;

55) (+−)-Trans-1-(3-ethyl-2,3,4,5-tetrahydro-8-methoxy-5-phenyl-1,4-benzothiazepin-3-yl)-4,4,4-trifluoro-1-butanol S,S-dioxide;

56) (+−)-Trans-1-(3-ethyl-2,3,4,5-tetrahydro-7,8-dimethoxy-5-phenyl-1,4-benzothiazepin-3-yl)-4,4,4-trifluoro-1-butanol S,S-dioxide;

57) (+−)-Trans-1-(3-Ethyl-2,3,4,5-tetrahydro-7,8-dihydroxy-5-phenyl-1,4-benzothiazepin-3-yl)-2-butanone S,S-dioxide

PHARMACEUTICAL COMPOSITION EXAMPLES

In the following Examples, the active compound can be any compound of formula (I) and/or a pharmaceutically acceptable salt, solvate, or physiologically functional derivative thereof. The active compound is preferably one of the compounds of synthetic examples 1 to 63.

(i) Tablet compositions

The following compositions A and B can be prepared by wet granulation of ingredients (a) to (c) and (a) to (d) with a solution of povidone, followed by addition of the magnesium stearate and compression.

| Composition A | mg/tablet | mg/tablet |
|---|---|---|
| (a) Active ingredient | 250 | 250 |
| (b) Lactose B.P. | 210 | 26 |
| (c) Sodium Starch Glycollate | 20 | 12 |
| (d) Povidone B.P. | 15 | 9 |
| (e) Magnesium Stearate | 5 | 3 |
| | 500 mg/tablet | 300 mg/tablet |
| Composition B | | |
| (a) Active ingredient | 250 | 250 |
| (b) Lactose | 150 | 150 |
| (c) Avicel PH 101 | 60 | 26 |
| (d) Sodium Starch Glycollate | 20 | 12 |
| (e) Povidone B.P. | 15 | 9 |
| (f) Magnesium Stearate | 5 | 3 |
| | 500 | 300 |
| Composition C | mg/tablet | |
| Active ingredient | 100 | |
| Lactose | 200 | |
| Starch | 50 | |
| Povidone | 5 | |
| Magnesium Stearate | 4 | |
| | 359 | |

The following compositions D and E can be prepared by direct compression of the admixed ingredients. The lactose used in composition E is of the direct compression type.

| | tablet/mg |
|---|---|
| Composition D | |
| Active ingredient | 250 |
| Magnesium Stearate | 4 |

| | tablet/mg |
|---|---|
| Pregelatinised Starch NF15 | 146 |
| | 400 |

Composition E

| | |
|---|---|
| Active ingredient | 250 |
| Magnesium Stearate | 5 |
| Lactose | 145 |
| Avicel | 100 |
| | 500 |

| Composition F (Controlled release composition) | mg/tablet |
|---|---|
| (a) Active ingredient | 500 |
| (b) Hydroxypropylmethylcellulose (Methocel K4M Premium) | 112 |
| (c) Lactose B.P. | 53 |
| (d) Povidone B.P.C. | 28 |
| (e) Magnesium Stearate | 7 |
| | 700 |

The composition can be prepared by wet granulation of ingredients (a) to (c) with a solution of povidone, followed by addition of the magnesium stearate and compression.

Composition G (Enteric-coated tablet)

Enteric-coated tablets of Composition C can be prepared by coating the tablets with 25 mg/tablet of an enteric polymer such as cellulose acetate phthalate, polyvinylacetate phthalate, hydroxypropylmethyl-cellulose phthalate, or anionic polymers of methacrylic acid and methacrylic acid methyl ester (Eudragit L). Except for Eudragit L, these polymers should also include 10% (by weight of the quantity of polymer used) of a plasticizer to prevent membrane cracking during application or on storage. Suitable plasticizers include diethyl phthalate, tributyl citrate and triacetin.

Composition H (Enteric-coated controlled release tablet)

Enteric-coated tablets of Composition F can be prepared by coating the tablets with 50 mg/tablet of an entire polymer such as cellulose acetate phthalate, polyvinylacetate phthalate, hydroxypropylmethyl-cellulose phthalate, or anionic polymers of methacrylic acid and methacrylic acid methyl ester (Eudragit L). Except for Eudragit L, these polymers should also include 10% (by weight of the quantity of polymer used) of a plasticizer to prevent membrane cracking during application or on storage. Suitable plasticizers include diethyl phthalate, tributyl citrate and triacetin.

(ii) Capsule compositions

Composition A

Capsules can be prepared by admixing the ingredients of Composition D above and filling two-part hard gelatin capsules with the resulting mixture. Composition B (infra) can be prepared in a similar manner.

| | mg/capsule |
|---|---|
| Composition B | |
| (a) Active ingredient | 250 |
| (b) Lactose B.P. | 143 |
| (c) Sodium Starch Glycollate | 25 |
| (d) Magnesium Stearate | 2 |
| | 420 |

| | mg/capsule |
|---|---|
| Composition C | |
| (a) Active ingredient | 250 |
| (b) Macrogol 4000 BP | 350 |
| | 600 |

Capsules can be prepared by melting the Macrogol 4000 BP, dispersing the active ingredient in the melt and filling two-part hard gelatin capsules therewith.

| Composition D | mg/capsule |
|---|---|
| Active ingredient | 250 |
| Lecithin | 100 |
| Arachis Oil | 100 |
| | 450 |

Capsules can be prepared by dispersing the active ingredient in the lecithin and arachis oil and filling soft, elastic gelatin capsules with the dispersion.

| Composition E (Controlled release capsule) | mg/capsule |
|---|---|
| (a) Active ingredient | 250 |
| (b) Microcrystalline Cellulose | 125 |
| (c) Lactose BP | 125 |
| (d) Ethyl Cellulose | 13 |
| | 513 |

The controlled release capsule formulation can be prepared by extruding mixed ingredients (a) to (c) using an extruder, then spheronising and drying the extrudate. The dried pellets are coated with release controlling membrane (d) and filled into two-part, hard gelatin capsules.

| Composition F (Enteric capsule) | mg/capsule |
|---|---|
| (a) Active ingredient | 250 |
| (b) Microcrystalline Cellulose | 125 |
| (c) Lactose BP | 125 |
| (d) Cellulose Acetate Phthalate | 50 |
| (e) Diethyl Phthalate | 5 |
| | 555 |

The entire capsule composition can be prepared by extruding mixed ingredients (a) to (c) using an extruder, then spheronising and drying the extrudate. The dried pellets are coated with an enteric membrane (d) containing a plasticizer (e) and filled into two-part, hard gelatin capsules.

Composition G (Enteric-coated controlled release capsule)

Enteric capsules of Composition E can be prepared by coating the controlled-release pellets with 50 mg/capsule of an enteric polymer such as cellulose acetate phthalate, polyvinylacetate phthalate, hydroxypropylmethylcellulose phthalate, or anionic polymers of methacrylic acid and methacrylic acid methyl ester (Eudgragit L). Except for Eudragit L, these polymers should also include 10% (by weight of the quantity of polymer used) of a plasticizer to prevent membrane cracking during application or on storage. Suitable plasticizers include diethyl phthalate, tributyl citrate and triacetin.

| (iii) Intravenous infection composition | |
|---|---|
| Active ingredient | 0.200 g |
| Sterile, pyrogen-free phosphate buffer (pH 9.0) to | 10 ml |

The active ingredient is dissolved in most of the phosphate buffer at 35°–40° C., then made up to volume and filtered through a sterile micropore filter into sterile 10 ml glass vials (Type 1) which are sealed with sterile closures and overseals.

| (iv) Intramuscular injection composition | |
|---|---|
| Active ingredient | 0.20 g |
| Benzyl Alcohol | 0.10 g |
| Glycofurol 75 | 1.45 g |
| Water for Injection | q.s. to 3.00 ml |

The active ingredient is dissolved in the glycofurol. The benzyl alcohol is then added and dissolved, and water added to 3 ml. The mixture is then filtered through a sterile micropore filter and sealed in sterile 3 ml glass vials (Type 1).

| (v) Syrup composition | |
|---|---|
| Active ingredient | 0.25 g |
| Sorbitol Solution | 1.50 g |
| Glycerol | 1.00 g |
| Sodium Benzoate | 0.005 g |
| Flavour | 0.0125 ml |
| Purified Water | q.s. to 5.0 ml |

The sodium benzoate is dissolved in a portion of the purified water and the sorbitol solution added. The active ingredient is added and dissolved. The resulting solution is mixed with the glycerol and then made up to the required volume with the purified water.

| (vi) Suppository composition | mg/suppository |
|---|---|
| Active ingredient | 250 |
| Hard Fat. BP (Witepsol H15 - Dynamit NoBel) | 1770 |
| | 2020 |

One-fifth of the Witepsol H15 is melted in a steam-jacketed pan at 45° C. maximum. The active ingredient is shifted through a 200 ml sieve and added to the molten base with mixing, using a Silverson fitted with a cutting head, until a smooth dispersion is achieved. Maintaining the mixture at 45° C., the remaining Witepsol H15 is added to the suspension which is stirred to ensure a homogenous mix. The entire suspension is then passed through a 250 ml stainless steel screen and, with continuous stirring, allowed to cool to 40° C. At a temperature of 38°–40° C., 2.02 g aliquots of the mixture are filled into suitable plastic moulds and the suppositories allowed to cool to room temperature.

| (vii) Pessary composition | mg/pessary |
|---|---|
| Active ingredient (631 m) | 250 |
| Anhydrous Dextrose | 380 |

-continued

| (vii) Pessary composition | mg/pessary |
|---|---|
| Potato Starch | 363 |
| Magnesium Stearate | 7 |
| | 1000 |

The above ingredients are mixed directly and pessaries prepared by compression of the resulting mixture.

| (viii) Transdermal composition | |
|---|---|
| Active ingredient | 200 mg |
| ALcohol USP | 0.1 ml |
| Hydroxyethyl cellulose | |

The active ingredient and alcohol USP are gelled with hydroxyethyl cellulose and packed in a transdermal device with a surface area of 10 cm$^2$.

Biological Assay

In vitro inhibition of bile acid uptake

Freshly prepared rat distal ileal brush border membrane vesicles (about 200 mg vesicle protein) were incubated for 30 seconds at 24° C. in an incubation mixture comprising 101M $^3$H taurocholate, 100 mM NaCl (or KCl) and 80 mM mannitol in 20 mM Hepes Tris pH 7.4. Each test compound was dissolved in ethanol (or water) and then diluted with incubation mixture to an ethanol concentration of not more than 1% v/v. The incubation was terminated by rapid dilution and filtration and the filter washed with an ice-cold isotonic sodium-free buffer.

The uptake of $^3$H taurocholate was measured by the radioactivity remaining on the filter and converted to pmoles/mg vesicle protein. The active, ie sodium-dependent, uptake was obtained by subtracting the passive uptake measured in 100 mM KCl from the total uptake measured in 100 mM NaCl. The active uptake for each test compound was compared with a control active uptake and the results expressed as % inhibition of bile acid uptake.

Data is given below for % inhibition of bile acid uptake at various concentrations of compounds of the invention.

| Example | 10 μM | 3 μM | 1 μM | 0.3 μM |
|---|---|---|---|---|
| 11 | 85 | 63 | 31 | 13 |
| 12 | 95 | 86 | 72 | 47 |
| 2 | 83 | 60 | 44 | 22 |
| 10 | 96 | 79 | 41 | 23 |
| 1 | 69 | 36 | | |
| 8 | 70 | 51 | 31 | 19 |
| 9 | 27 | 16 | 15 | |
| 24 | 23 | | | |

We claim:

1. A compound of formula (I):

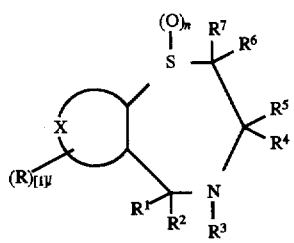

wherein l is an integer of from 0 to 4;

n is an integer of from 0 to 2;

R is an atom or group selected from halogen, cyano, hydroxy, nitro, alkyl, alkoxy, aryl, heteroaryl, aryloxy, arylalkoxy, aralkyl, alkaryl, —O(CH$_2$)$_p$SO$_3$R$^1$, —O(CH$_2$)$_p$NR$^{11}$R$^{12}$, —COR$^{11}$, —CO$_2$R$^{11}$, —CONR$^{11}$R$^{12}$, —CH$_2$OR$^{11}$, —NR$^{11}$R$^{12}$, —NHCOR$^{11}$, —NHSO$_2$R$^{11}$, —SR$^{11}$, —SO$_2$R$^{11}$, —SO$_2$NR$^{11}$R$^{12}$ and —SO$_3$R$^{11}$; or R is a group —OCH$_2$O— which forms a further ring attached to X;

wherein:

said alkyl, alkoxy, aryl, heteroaryl, aryloxy, arylalkoxy, aralkyl and alkaryl groups are optionally substituted by one or more atoms or groups independantly selected from halogen, hydroxy, nitro, nitrile, alkyl, alkoxy, —COR$^{11}$, —CO$_2$R$^{11}$, —SO$_3$R$^{11}$ and —NR$^{14}$R$^{15}$;

p is an integer of from 1 to 4;

R$^{11}$ and R$^{12}$ are independently selected from hydrogen, C$_{1-6}$ alkyl and phenyl; and R$^{14}$ and R$^{15}$ are independantly selected from hydrogen and C$_{1-6}$ alkyl;

R$^1$ is hydrogen or C$_{1-6}$ alkyl;

R$^2$ is an atom or group selected from hydrogen, C$_{1-6}$ alkyl (including cycloalkyl and cycloalkylalkyl), C$_{1-4}$ alkoxy, pyrryl, thienyl, pyridyl, 1,3-benzodioxolo, phenyl and naphthyl, which groups are optionally substituted by one or more atoms or groups independently selected from halogen, cyano, hydroxy, nitro, carboxyl, phenyl, phenoxy, benzyloxy, —COR$^{11}$, —CO$_2$R$^{11}$, —CONR$^{11}$R$^{12}$, —CH$_2$OR$^{11}$, —NR$^{11}$R$^{12}$, —NHCOR$^{11}$, —NHSO$_2$R$^{11}$, —SR$^{11}$, —SO$_2$R$^{11}$, —SO$_3$R$^{11}$, —O(CH$_2$)$_p$NR$^{11}$R$^{12}$, and —O(CH$_2$)$_p$SO$_3$R$^{11}$ (wherein p, R$^{11}$ and R$^{12}$ are as hereinbefore defined);

R$^3$ is hydrogen, hydroxy C$_{1-6}$ alkyl, alkoxy or —O—C$_{1-6}$ alkanoyl;

R$^4$ is a group selected from C$_{1-6}$ alkyl (including cycloalkyl and cycloalkylalkyl), C$_{2-6}$ alkenyl, and C$_{2-6}$ alkynyl, which groups are optionally substituted by one or more atoms or groups independently selected from halogen, oxo, —OR$^{14}$, —CO$_2$R$^{14}$, —NR$^{14}$R$^{15}$, —SR$^{14}$, —S(O)C$_{1-6}$ alkyl, —SO$_2$R$^{14}$ and —SO$_3$R$^{14}$;

R$^5$ is a group selected from C$_{2-6}$ alkyl (including cycloalkyl and cycloalkylalkyl), C$_{2-6}$ alkenyl and C$_{2-6}$ alkynyl, which groups are optionally substituted by one or more atoms or groups independently selected from halogen, oxo, —OR$^{14}$, —CO$_2$R$^{14}$, —NR$^{14}$R$^{15}$, —SR$^{14}$, —S(O)C$_{1-6}$ alkyl, —SO$_2$R$^{14}$ and —SO$_3$R$^{14}$ (wherein R$^{14}$ and R$^{15}$ are as hereinbefore defined);

or R$^4$ and R$^5$, together with the carbon atom to which they are attached, form a C$_{3-7}$ spiro cycloalkyl group which is optionally substituted by one or more atoms or groups independently selected from halogen, —OR$^{14}$, —CO$_2$R$^{14}$, —SO$_3$R$^{14}$ and —NR$^{14}$R$^{15}$ (wherein R$^{14}$ and R$^{15}$ are as hereinbefore defined);

R$^6$ and R$^7$ are independently selected from hydrogen and C$_{1-6}$ alkyl;

X is an aromatic or non-aromatic monocyclic or bicyclic ring system having from 5 to 10 carbon atoms (including the two carbon atoms forming part of the thiazepine ring) or X is a fused pyrryl, thienyl, or pyridyl group;

with the proviso that at least one of R, R$^2$, R$^4$ and R$^5$ is hydroxy or a group containing hydroxy; and salts and solvates thereof.

2. A compound as claimed in claim 1 wherein l is an integer of from 0 to 4;

n is an integer of from 0 to 2;

R is an atom or group selected from halogen, cyano, hydroxy, nitro, alkyl, alkoxy, aryl, heteroaryl, aryloxy, arylalkoxy, aralkyl, alkaryl, —COR$^{11}$, —CO$_2$R$^{11}$, —CONR$^{11}$R$^{12}$, —CH$_2$OR$^{11}$, —NR$^{11}$R$^{12}$, —NHCOR$^{11}$, —NHSO$_2$R$^{11}$, —SR$^{11}$, —SO$_2$R$^{11}$ and —SO$_3$R$^{11}$;

wherein:

said alkyl, alkoxy, aryl, heteroaryl, aryloxy, arylalkoxy, aralkyl and alkaryl groups are optionally substituted by one or more atoms or groups independantly selected from halogen, hydroxy, nitro, nitrile, alkyl, alkoxy, —COR$^{11}$, —CO$_2$R$^{11}$, —SO$_3$R$^{11}$ and —NR$^{14}$R$^{15}$;

R$^{11}$ and R$^{12}$ are independently selected from hydrogen, C$_{1-6}$ alkyl and phenyl; and R$^{14}$ and R$^{15}$ are independantly selected from hydrogen and C$_{1-6}$ alkyl;

R$^1$ is hydrogen or C$_{1-6}$ alkyl;

R$^2$ is an atom or group selected from hydrogen, C$_{1-6}$ alkyl (including cycloalkyl and cycloalkylalkyl), C$_{1-4}$ alkoxy, pyrryl, thienyl, pyridyl, 1,3-benzodioxolo, phenyl and naphthyl, which groups are optionally substituted by one or more atoms or groups independently selected from halogen, cyano, hydroxy, nitro, carboxyl, phenyl, phenoxy, benzyloxy, —COR$^{11}$, —CO$_2$R$^{11}$, —CONR$^{11}$R$^{12}$, —CH$_2$OR$^{11}$, —NR$^{11}$R$^{12}$, —NHCOR$^{11}$, —NHSO$_2$R$^{11}$, —SR$^{11}$, —SO$_2$R$^{11}$, —SO$_3$R$^{11}$, —O(CH$_2$)$_p$NR$^{11}$R$^{12}$, and —O(CH$_2$)$_p$SO$_3$R$^{11}$ (wherein p is an integer of from 1 to 4, and R$^{11}$ and R$^{12}$ are as hereinbefore defined);

R$^3$ is selected from hydrogen, hydroxy and C$_{1-6}$ alkyl;

R$^4$ is a group selected from C$_{1-6}$ alkyl (including cycloalkyl and cycloalkylalkyl), C$_{2-6}$ alkenyl and C$_{2-6}$ alkynyl, which groups are optionally substituted by one or more atoms or groups independently selected from halogen, —OR$^{14}$, —CO$_2$R$^{14}$, —NR$^{14}$R$^{15}$ and —SO$_3$R$^{14}$ (wherein R$^{14}$ and R$^{15}$ are as hereinbefore defined);

R$^5$ is a group selected from C$_{2-6}$ alkyl (including cycloalkyl and cycloalkylalkyl), C$_{2-6}$ alkenyl and C$_{2-6}$ alkynyl, which groups are optionally substituted by one or more atoms or groups independently selected from halogen, —OR$^{14}$, —CO$_2$R$^{14}$, —NR$^{14}$R$^{15}$ and —SO$_3$R$^{14}$ (wherein R$^{14}$ and R$^{15}$ are as hereinbefore defined);

or R$^4$ and R$^5$, together with the carbon atom to which they are attached, form a C$_{3-7}$ spiro cycloalkyl group which is optionally substituted by one or more atoms or groups independently selected from halogen, —$OR^{14}$, —$CO_2R^{14}$, —$SO_3R^{14}$ and —$NR^{14}R^{15}$ (where $R^{14}$ and $R^{15}$ are as hereinbefore defined);

$R^6$ and $R^7$ are independently selected from hydrogen and $C_{1-6}$ alkyl;

X is an aromatic or non-aromatic monocyclic or bicyclic ring system having from 5 to 10 carbon atoms (including the two carbon atoms forming part of the thiazepine ring) or X is a fused pyrryl, thienyl, or pyridyl group;

with the proviso that at least one of R, $R^2$, $R^4$ and $R^5$ is hydroxy or a group containing hydroxy; and salts and solvates thereof.

3. A compound as claimed in claim 1 wherein:

l is 0, 1, or 2;

n is 1 or 2; and $R^1$, $R^6$ and $R^7$ are all hydrogen; and $R^3$ is hydrogen or hydroxy.

4. A compound as claimed in claim 1 which is:

(±)-trans-3-ethyl-2,3,4,5-tetrahydro-3-((2R)-2-hydroxybutyl)-5-phenyl-1,4-benzothiazepine 1,1-dioxide;

(±)-trans-1-(3-ethyl-2,3,4,5-tetrahydro-8-methoxy-5-phenyl-1,4-benzothiazepin-3-yl)-2(R)-2-butanol S,S-dioxide;

(±)-trans-1-(3-ethyl-2,3,4,5-tetrahydro-8-methoxy-5-phenyl-1,4-benzothiazepin-3-yl)-3-butanol S,S-dioxide;

(±)-trans-1-(3-ethyl-2,3,4,5-tetrahydro-7-methoxy-5-phenyl-1,4-benzothiazepin-3-yl)-2(R)-2-butanol S,S-dioxide;

(±)-trans-1-(3-ethyl-5-(4-fluorophenyl)-2,3,4,5-tetrahydro-7-methoxy-1,4-benzothiazepin-3-yl)-2(R)-2-butanol S,S-dioxide;

(±)-trans-1-(3-ethyl-5-(4-hydroxyphenyl)-2,3,4,5-tetrahydro-1,4-benzothiazepin-3-yl)-2(R)-2-butanol S,S-dioxide 0.5 hydrate;

(±)-trans-3-butyl-3-ethyl-2,3,4,5-tetrahydro-5-(4-hydroxyphenyl)-1,4-benzothiazepine 1,1-dioxide hydrochloride;

(±)-cis-3-ethyl-2,3,4,5-tetrahydro-3-(4-hydroxybutyl)-5-phenyl-1,4-benzothiazepine 1,1-dioxide hydrochloride;

(±)-trans-3-ethyl-2,3,4,5-tetrahydro-3-(4-hydroxybutyl)-5-phenyl-1,4-benzothiazepine 1,1-dioxide;

(±)-trans-3-butyl-3-ethyl-2,3,4,5-tetrahydro-7-hydroxy-5-phenyl-1,4-benzothiazepine 1,1-dioxide;

(±)-trans-1-(3-ethyl-2,3,4,5-tetrahydro-5-phenyl-1,4-benzothiazepin-3-yl)-4,4,4-trifluoro-(2S)-2-butanol-S,S-dioxide;

(±)-trans-1-(3-ethyl-2,3,4,5-tetrahydro-7-methoxy-5-phenyl-1,4-benzothiazepin-3-yl)-4,4,4-trifluoro-(2S)-2-butanol-S,S-dioxide;

(±)-trans-3-Ethyl-2,3,4,5-tetrahydro-3-(3-hydroxybutyl)-5-phenyl-1,4-benzothiazepine 1,1-dioxide;

(±)-trans-3-Ethyl-2,3,4,5-tetrahydro-3-(2(R)-2-hydroxybutyl)-5-(4-hydroxyphenyl)-1,4-benzothiazepine 1,1-dioxide;

(±)-trans-1-(3-Ethyl-5-(4-fluorophenyl)-2,3,4,5-tetrahydro-1,4-benzothiazepin-3-yl)-2(R)-2-butanol S,S-dioxide;

(±)-trans-1-(3-Ethyl-2,3,4,5-tetrahydro-7-methoxy-5-phenyl-1,4-benzothiazepin-3-yl)-4,4,4-trifluoro-2(S)-2-butanol S,S-dioxide;

(±)-trans-1-(3-Ethyl-2,3,4,5-tetrahydro-8-methoxy-5-phenyl-1,4-benzothiazepin-3-yl)-4,4,4-trifluoro-2(S)-butanol S,S-dioxide;

(±)-trans-1-(3-ethyl-23,4,5-tetrahydro-7,8-dimethoxy-5-phenyl-1,4-benzothiazepin-3-yl)-2(R)-2-butanol S,S dioxide;

(±)-trans-1-(3-Ethyl-2,3,4,5-tetrahydro-7,8-dimethoxy-5-phenyl-1,4-benzothiazepin-3-yl)-4,4,4-trifluoro-2-butanol S,S-dioxide;

(±)-trans-1-(3-Ethyl-2,3,4,5-tetrahydro-7,8-dimethoxy-5-phenyl-1,4-benzothiazepin-3-yl)-3,3,4,4,4-pentafluoro-2-butanol S,S-dioxide;

(±)-trans-3-((3-ethyl-2,3,4,5-tetrahydro-5-phenyl-3-(4,4,4-trifluoro-2-hydroxybutyl)-1,4-benzothiazepin-8-yl)oxy)propanesulfonic acid, 1,1-dioxide;

(±)-trans-3-((3-ethyl-2,3,4,5-tetrahydro-3-(2-hydroxybutyl)-5-phenyl-1,4-benzothiazepin-8-yl)oxy)ethyltrimethylammonium iodide 1,1-dioxide;

(±)-trans-1-(3-Ethyl-2,3,4,5-tetrahydro-7,8-diethoxy-5-phenyl-1,4-benzothiazepin-3-yl)-4,4,4-trifluoro-2-butanol S,S-dioxide;

(±)-trans-3-((3-ethyl-2,3,4,5-tetrahydro-5-phenyl-3(4,4,4-trifluoro-2-hydroxybutyl)-1,4-benzothiazepin-8-yl)oxy)ethyltrimethylammonium iodide 1,1-dioxide;

(±)-trans-3-((3-ethyl-2,3,4,5-tetrahydro-3-(2-hydroxybutyl)-5-phenyl-1,4-benzothiazepin-8-yl)oxy)propanesulfonic acid 1,1-dioxide;

(±)-trans-1-(3-ethyl-2,3,4,5-tetrahydro-7,8-diethoxy-5-phenyl-1,4-benzothiazepin-3-yl)-2-butanol S,S-dioxide;

(±)-trans-1-(3-(2,2,2-trifluoroethyl)-2,3,4,5-tetrahydro-7,8-dimethoxy-5-phenyl-1,4-benzothiazepin-3-yl)-4,4,4-trifluoro-2-butanol S,S-dioxide;

(±)-trans-1-(3-Ethyl-2,3,4,5-tetrahydro-7,8-dihydroxy-5-phenyl-1,4-benzothiazepin-3-yl)-4,4,4-trifluoro-2-butanol S,S-dioxide;

(±)-trans-1-(3-ethyl-2,3,4,5-tetrahydro-7,8-dimethoxy-5-phenyl-1,4-benzothiazepin-3-yl)-1-butanol S,S-dioxide;

(±)-trans-1-(3-Ethyl-2,3,4,5-tetrahydro-7,8-dihydroxy-5-phenyl-1,4-benzothiazepin-3-yl)-2-butanol S,S-dioxide;

(±)-trans-1-(3-ethyl-2,3,4,5-tetrahydro-8-methoxy-5-phenyl-1,4-benzothiazepin-3-yl)-4,4,4-trifluoro-1-butanol S,S-dioxide; or (±)-trans-1-(3-ethyl-2,3,4,5-tetrahydro-7,8-dihydroxy-5-phenyl-1,4-benzothiazepin-3-yl)-2-butanone S,S-dioxide.

5. A compound as claimed in claim 1 which is:

(±)-tans-1-(3-ethyl-5-(4-fluorophenyl)-2,3,4,5-tetrahydro-7-methoxy-1,4-benzothiazepin-3-yl)-2(R)-2-butanol S,S-dioxide;

(±)-trans-1-(3-ethyl-2,3,4,5-tetrahydro-5-phenyl-1,4-benzothiazepin-3-yl)-4,4,4-trifluoro-(2S)-2-butanol-S,S-dioxide;

(±)-trans-1-(3-ethyl-2,3,4,5-tetrahydro-7-methoxy-5-phenyl-1,4-benzothiazepin-3-yl)-4,4,4-trifluoro-(2S)-2-butanol-S,S-dioxide;

(±)-trans-1-(3-Ethyl-2,3,4,5-tetrahydro-8-methoxy-5-phenyl-1,4-benzothiazepin-3-yl)-4,4,4-trifluoro-2(S)-butanol S,S-dioxide; or (±)-trans-1-(3-ethyl-23,4,5-tetrahydro-7,8-dimethoxy-5-phenyl-1,4-benzothiazepin-3-yl)-2(R)-2-butanol S,S dioxide.

6. A pharmaceutical composition comprising the compound as claimed in claim 1 together with one or more parmacuetically acceptable carriers.

7. A method of treating a mammal for a hyperlipidemic condition or atherosclerosis, comprising administering to the mammal an effective treatment amount of the pharmaceutical composition of claim 6.

8. A method according to claim 7 wherein the mammal is a human.

9. A method of inhibiting bile acid absorbtion of bile acids from the intestine of a mammal comprising administering to the mammal an effective bile acid absorption inhibiting amount of the pharmaceutical composition of claim 6.

10. A method according to claim 9 wherein the mammal is a human.

11. A method of treating a mammal by reducing blood plasma or serum concentrations of LDL or VLDL, or reducing cholesterol and cholesterol ester in the blood plasma or serum, in a mammal comprising administering to the mammal an effective reducing amount of the pharmaceutical composition of claim 6.

12. A method according to claim 11 wherein the mammal is a human.

13. A method of increasing fecal excretions of bile acids in a mammal comprising administering to the mammal an effective fecal excretion amount of the pharmaceutical composition of claim 6.

14. A process for the preparation of the compound as claimed in claim 1 which comprises at least the step of:

(a) Wherein n=0 and $R^1$ and $R^3$ are hydrogen, reducing the imine bond of a compound of formula (II):

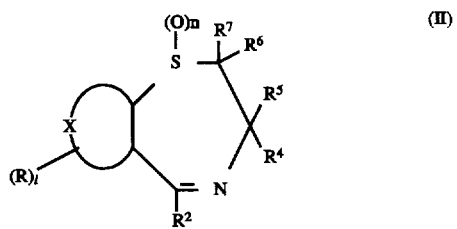

wherein 1, n, R, $R^2$, $R^4$ to $R^7$ and X are as hereinbefore defined: or (b) wherein n=0 and $R^1$ is not hydrogen, by alkylation of the corresponding compound of formula (II); or (c) wherein n=0 and $R^3$ is hydrogen, by cyclising a compound of formula (VIII):

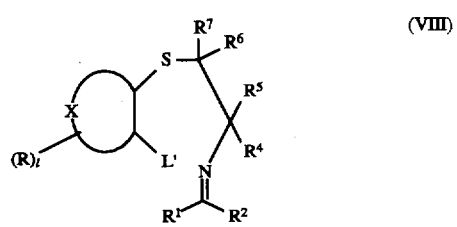

wherein 1, R, $R^2$, $R^4$ to $R^7$ and X are as hereinbefore defined and $L^1$ is halogen, by treatment with a strong base; or (d) wherein n=0 and $R^1$ and $R^3$ are both hydrogen, alkylating a compound of formula (XIII)

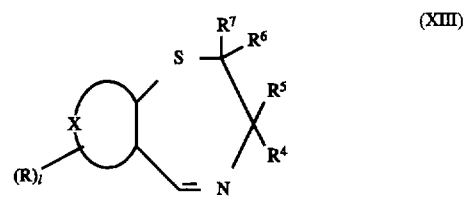

wherein 1, R, $R^2$, $R^4$ to $R^7$ and X are as hereinbefore defined; or (e) by reaction of a compound of formula (I) wherein $R^4$ is $C_{2-6}$ alkenyl with gaseous hydrogen halide to give the corresponding compound of formula (I) wherein $R^4$ is halogen substituted $C_{2-6}$ alkyl, optionally followed by a hydrolysis step using $H_2O_2$ to give the corresponding compound of formula (I) wherein $R^4$ is hydroxy substituted $C_{2-6}$ alkyl; or (f) by reduction and hydroxylation of a compound of formula (II) wherein $R^4$ is $C_{2-6}$ alkenyl; or (g) by hydrogenation of a compound of formula (II) wherein $R^4$ is hydroxy substituted $C_{2-6}$ alkenyl; or (h) by debenzylation of a compound of formula (I) wherein $R^2$ is benzyloxyphenyl; or (i) wherein n=0 and $R^3$ is not hydrogen, by N-alkylation of the corresponding compound of formula (II) with an alkyl halide, followed by reduction to a compound of formula (I); or (j) wherein n is 1 or 2 oxidation of the corresponding compound of formula (I) wherein n is 0; or (k) wherein n is 1 or 2, oxidation of the corresponding compound of formula (II) wherein n is 0 prior to cyclisation and reduction to the compound of formula (I).

15. A compound of formula (II):

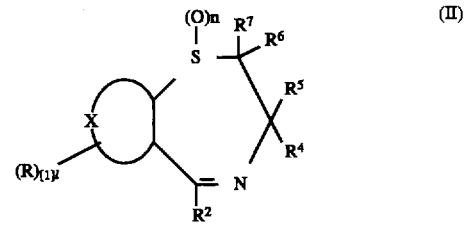

wherein:

l is an integer of from 0 to 4;

n is an integer of from 0 to 2;

R is an atom or group selected from halogen, cyano, hydroxy, nitro, alkyl, alkoxy, aryl, heteroaryl, aryloxy, arylalkoxy, aralkyl, alkaryl, —O(CH$_2$)$_p$SO$_3$R$^{11}$, —O(CH$_2$)$_p$NR$^{11}$R$^{12}$, —COR$^{11}$, —CO$_2$R$^{11}$, —CONR$^{11}$R$^{12}$, —CH$_2$OR$^{11}$, —NR$^{11}$R$^{12}$, —NHCOR$^{11}$, —NHSO$_2$R$^{11}$, —SR$^{11}$, —SO$_2$R$^{11}$, —SO$_2$NR$^{11}$R$^{12}$ and —SO$_3$R$^{11}$; or R is a group —OCH$_2$O— which forms a further ring attached to X;

wherein:

said alkyl, alkoxy, aryl, heteroaryl, aryloxy, arylalkoxy, aralkyl and alkaryl groups are optionally substituted by one or more atoms or groups independantly selected from halogen, hydroxy, nitro, nitrile, alkyl, alkoxy, —COR$^{11}$, —CO$_2$R$^{11}$, —SO$_3$R$^{11}$ and —NR$^{14}$R$^{15}$;

p is an integer of from 1 to 4;

$R^{11}$ and $R^{12}$ are independently selected from hydrogen, $C_{1-6}$ alkyl and phenyl; and $R^{14}$ and $R^{15}$ are independantly selected from hydrogen and $C_{1-6}$ alkyl;

$R^2$ is an atom or group selected from hydrogen, $C_{1-6}$ alkyl (including cycloalkyl and cycloalkylalkyl), $C_{1-4}$ alkoxy, pyrryl, thienyl, pyridyl, 1,3-benzodioxolo, phenyl and naphthyl, which groups are optionally substituted by one or more atoms or groups independently selected from halogen, cyano, hydroxy, nitro, carboxyl, phenyl, phenoxy, benzyloxy, —$COR^{11}$, —$CO_2R^{11}$, —$CONR^{11}R^{12}$, —$CH_2OR^{11}$, —$NR^{11}R^{12}$, —$NHCOR^{11}$, —$NHSO_2R^{11}$, —$SR^{11}$, —$SO_2R^{11}$, —$SO_3R^{11}$, —$O(CH_2)_pNR^{11}R^{12}$, and —$O(CH_2)_pSO_3R^{11}$ (wherein p is an integer of from 1 to 4, and $R^{11}$ and $R^{12}$ are as hereinbefore defined);

$R^4$ is a group selected from $C_{1-6}$ alkyl (including cycloalkyl and cycloalkylalkyl), $C_{2-6}$ alkenyl, and $C_{2-6}$ alkynyl, which groups are optionally substituted by one or more atoms or groups independently selected from halogen, oxo, —$OR^{14}$, —$CO_2R^{14}$, —$NR^{14}R^{15}$, —$SR^{14}$, —$S(O)C_{1-6}$ alkyl, —$SO_2R^{14}$ and —$SO_3R^{14}$ (wherein $R^{14}$ and $R^{15}$ are as hereinbefore defined);

$R^5$ is a group selected from $C_{2-6}$ alkyl (including cycloalkyl and cycloalkylalkyl), $C_{2-6}$ alkenyl and $C_{2-6}$ alkynyl, which groups are optionally substituted by one or more atoms or groups independently selected from halogen, oxo, —$OR^{14}$, —$CO_2R^{14}$, —$NR^{14}R^{15}$, —$SR^{14}$, —$S(O)C_{1-6}$ alkyl, —$SO_2R^{14}$ and —$SO_3R^{14}$ (wherein $R^{14}$ and $R^{15}$ are as hereinbefore defined);

or $R^4$ and $R^5$, together with the carbon atom to which they are attached, form a $C_{3-7}$ spiro cycloalkyl group which is optionally substituted by one or more atoms or groups independently selected from halogen, —$OR^{14}$, —$CO_2R^{14}$, —$SO_3R^{14}$ and —$NR^{14}R^{15}$ (wherein $R^{14}$ and $R^{15}$ are as hereinbefore defined);

$R^6$ and $R^7$ are independently selected from hydrogen and $C_{1-6}$ alkyl;

X is an aromatic or non-aromatic monocyclic or bicyclic ring system having from 5 to 10 carbon atoms (including the two carbon atoms forming part of the thiazepine ring) or X is a fused pyrryl, thienyl, or pyridyl group;

with the proviso that at least one of R, $R^2$, $R^4$ and $R^5$ is hydroxy or a group containing hydroxy; and salts and solvates thereof.

16. A compound as claimed in claim 15 wherein:

l is an integer of from 0 to 4;

n is an integer of from 0 to 2;

R is an atom or group selected from halogen, cyano, hydroxy, nitro, alkyl, alkoxy, aryl, heteroaryl, aryloxy, arylalkoxy, aralkyl, alkaryl, —$COR^{11}$, —$CO_2R^{11}$, —$CONR^{11}R^{12}$, —$CH_2OR^{11}$, —$NR^{11}R^{12}$, —$NHCOR^{11}$, —$NHSO_2R^{11}$, —$SR^{11}$, —$SO_2R^{11}$ and —$SO_3R^{11}$;

wherein:

said alkyl, alkoxy, aryl, heteroaryl, aryloxy, arylalkoxy, aralkyl and alkaryl groups are optionally substituted by one or more atoms or groups independantly selected from halogen, hydroxy, nitro, nitrile, alkyl, alkoxy, —$COR^{11}$, —$CO_2R^{11}$, —$SO_3R^{11}$ and —$NR^{14}R^{15}$;

$R^{11}$ and $R^{12}$ are independently selected from hydrogen, $C_{1-6}$ alkyl and phenyl; and $R^{14}$ and $R^{15}$ are independantly selected from hydrogen and $C_{1-6}$ alkyl;

$R^2$ is an atom or group selected from hydrogen, $C_{1-6}$ alkyl (including cycloalkyl and cycloalkylalkyl), $C_{1-4}$ alkoxy, pyrryl, thienyl, pyridyl, 1,3-benzodioxolo, phenyl and naphthyl, which groups are optionally substituted by one or more atoms or groups independently selected from halogen, cyano, hydroxy, nitro, carboxyl, phenyl, phenoxy, benzyloxy, —$COR^{11}$, —$CO_2R^{11}$, —$CONR^{11}R^{12}$, —$CH_2OR^{11}$, —$NR^{11}R^{12}$, —$NHCOR^{11}$, —$NHSO_2R^{11}$, —$SR^{11}$, —$SO_2R^{11}$, —$SO_3R^{11}$, —$O(CH_2)_pNR^{11}R^{12}$, and —$O(CH_2)_pSO_3R^{11}$ (wherein p is an integer of from 1 to 4, and $R^{11}$ and $R^{12}$ are as hereinbefore defined);

$R^4$ is a group selected from $C_{1-6}$ alkyl (including cycloalkyl and cycloalkylalkyl), $C_{2-6}$ alkenyl and $C_{2-6}$ alkynyl, which groups are optionally substituted by one or more atoms or groups independently selected from halogen, —$OR^{14}$, —$CO_2R^{14}$, —$NR^{14}R^{15}$ and —$SO_3R^{14}$ (wherein $R^{14}$ and $R^{15}$ are are hereinbefore defined);

$R^5$ is a group selected from $C_{2-6}$ alkyl (including cycloalkyl and cycloalkylalkyl), $C_{2-6}$ alkenyl and $C_{2-6}$ alkynyl, which groups are optionally substituted by one or more atoms or groups independently selected from halogen, —$OR^{14}$, —$CO_2R^{14}$, —$NR^{14}R^{15}$ and —$SO_3R^{14}$ (wherein $R^{14}$ and $R^{15}$ are are hereinbefore defined);

or $R^4$ and $R^5$, together with the carbon atom to which they are attached, form a $C_{3-7}$ spiro cycloalkyl group which is optionally substituted by one or more atoms or groups independently selected from halogen, —$OR^{14}$, —$CO_2R^{14}$, —$SO_3R^{14}$ and —$NR^{14}R^{15}$ (where $R^{14}$ and $R^{15}$ are as hereinbefore defined);

$R^6$ and $R^7$ are independently selected from hydrogen and $C_{1-6}$ alkyl;

X is an aromatic or non-aromatic monocyclic or bicyclic ring system having from 5 to 10 carbon atoms (including the two carbon atoms forming part of the thiazepine ring) or X is a fused pyrryl, thienyl, or pyridyl group;

with the proviso that at least one of R, $R^2$, $R^4$ and $R^5$ is hydroxy or a group containing hydroxy; and salts and solvates thereof.

17. A compound as claimed in claim 15 wherein:

l is 0, 1, or 2;

n is 1 or 2; and $R^6$ and $R^7$ are hydrogen.

* * * * *